US011622811B1

(12) United States Patent
Song et al.

(10) Patent No.: US 11,622,811 B1
(45) Date of Patent: Apr. 11, 2023

(54) HIP ARTHROPLASTY PLANNING AND TEMPLATE DESIGN

(71) Applicant: Omnes Medical Inc., Houston, TX (US)

(72) Inventors: Benjamin Sooil Song, Los Angeles, CA (US); Ilwhan Park, Katy, TX (US)

(73) Assignee: Omnes Medical, Inc., Houston, TX (US)

( * ) Notice: Subject to any disclaimer, the term of this patent is extended or adjusted under 35 U.S.C. 154(b) by 285 days.

(21) Appl. No.: 17/193,280

(22) Filed: Mar. 5, 2021

Related U.S. Application Data

(60) Provisional application No. 62/985,648, filed on Mar. 5, 2020.

(51) Int. Cl.
| | |
|---|---|
| *A61B 34/10* | (2016.01) |
| *A61B 17/17* | (2006.01) |
| *G06T 7/00* | (2017.01) |
| *G16H 30/40* | (2018.01) |
| *G16H 50/50* | (2018.01) |
| *G16H 20/40* | (2018.01) |
| *A61F 2/46* | (2006.01) |

(52) U.S. Cl.
CPC ............ *A61B 34/10* (2016.02); *A61B 17/175* (2013.01); *A61B 17/1717* (2013.01); *A61B 17/1746* (2013.01); *G06T 7/0014* (2013.01); *G16H 20/40* (2018.01); *G16H 30/40* (2018.01); *G16H 50/50* (2018.01); *A61B 2034/108* (2016.02); *A61F 2/4607* (2013.01); *A61F 2/4609* (2013.01); *G06T 2207/30008* (2013.01)

(58) Field of Classification Search
CPC ............ A61B 17/1717; A61B 17/1746; A61B 17/175; A61B 34/10
See application file for complete search history.

(56) References Cited

U.S. PATENT DOCUMENTS

2015/0245922 A1\* 9/2015 Park .................. A61B 17/1746
606/91

OTHER PUBLICATIONS

A.J. Wassef et al., "Use of an offset head center acetabular shell in difficult primary total hip arthroplasties", Annals of Translational Medicine, 2019, 7(4):75, 7 pages.
(Continued)

*Primary Examiner* — Samuel S Hanna
(74) *Attorney, Agent, or Firm* — Mark Protsik; Thomas Schneck

(57) ABSTRACT

A computer-aided method of pre-operative planning of hip joint replacement is provided for establishing, from patient-specific images, femoral and acetabular implant sizes and cut planes. Image slices of a patient's hip joint are obtained. Coordinate positions of selected femur and acetabulum points (e.g., femoral head center, major trochanter midpoint, femoral shaft midpoint, acetabular rim high points and lowest point) in the images are marked, which allows the planning tool to perform a best fit analysis to offer a range of suitable implant and surgical cut plane parameters for selection by a surgeon. Patient-specific surgical jigs can then be constructed for the proximal femur and acetabulum of the hip joint corresponding to a surgeon selection between standard, mini, short-stem, and resurfacing hip replacement components and in accord with the surgeon-selected parameters.

16 Claims, 41 Drawing Sheets

(56) References Cited

OTHER PUBLICATIONS

M. Scaglione et al., "Hip replacement in femoral head osteonecrosis: current concepts", Clinical Cases in Mineral and Bone Metabolism 2015, 12(Suppl. 1), pp. 51-54, 4 pages.

K. Issa et al., "Hip pathologies that bedevil—Osteonecrosis of the femoral head: The total hip replacement solution", CCJR Supplemental to the Bone & Joint Journal, vol. 95-B, No. 11, Nov. 2013, pp. 46-50, 5 pages.

V.C. Bose et al., "Resurfacing arthroplasty of the hip for avascular necrosis of the femoral head", The Journal of Bone and Joint Surgery, vol. 92-B, 922-8, Mar. 16, 2010, 7 pages.

\* cited by examiner

41

41

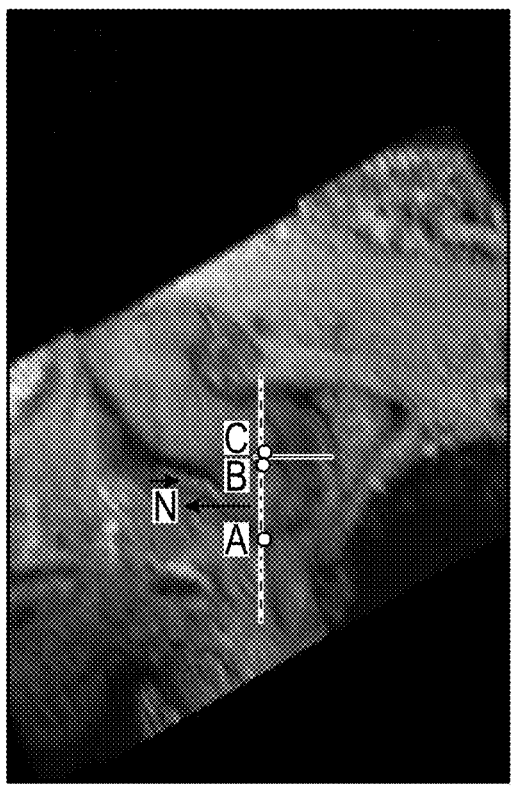 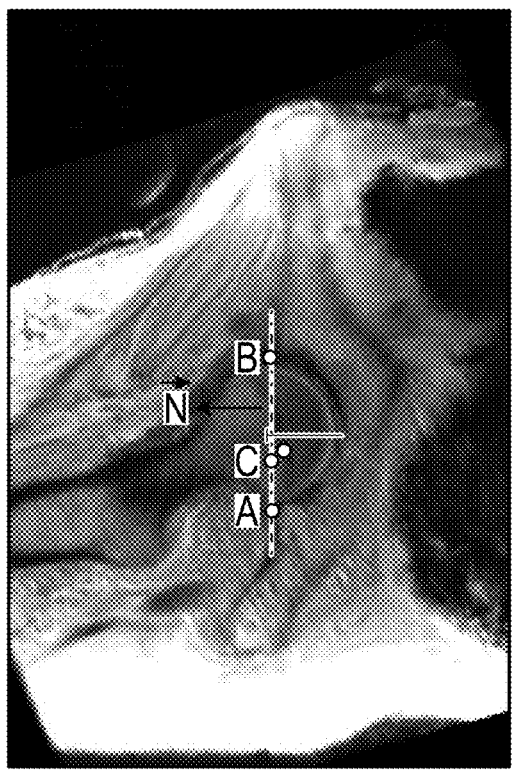
FIG. 13A    FIG. 13B
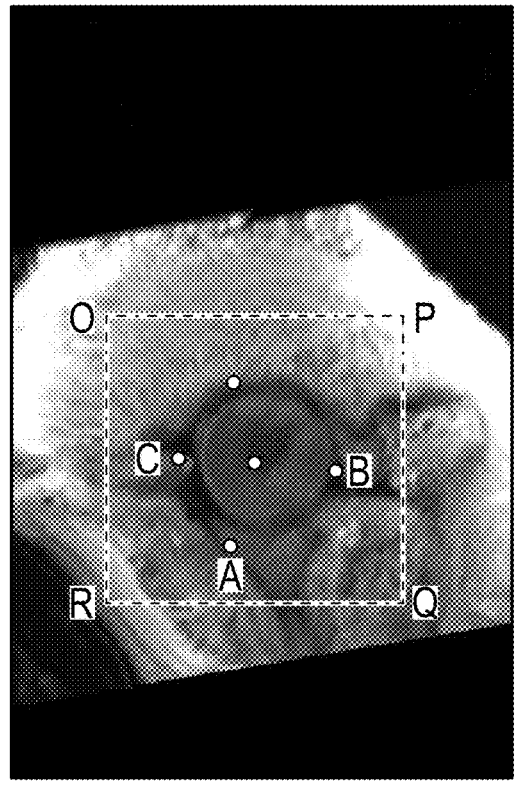
FIG. 13C

HIP ARTHROPLASTY PLANNING AND TEMPLATE DESIGN

CROSS-REFERENCE TO RELATED APPLICATION

This application claims priority under 35 U.S.C. 119(e) from U.S. provisional application 62/985,648 filed Mar. 5, 2020.

TECHNICAL FIELD

The invention relates to computer-aided hip replacement pre-planning, including patient-specific image-based tools with implant size selection and surgical cut plane estimation for hip replacement surgery.

BACKGROUND ART

Osteonecrosis (also known as avascular necrosis) is a chronic disease caused by reduced blood flow to bone tissue near the joints. In people with healthy bones, new bone is always replacing old bone. In osteonecrosis, the lack of blood causes the bone to break down faster than the body can make enough new bone. The bone starts to die and may break down. Severe cases of femoral neck osteonecrosis may not provide enough volume for the use of hip resurfacing implants, making total hip replacement necessary in such cases.

Pre-operative planning is an important step prior to hip replacement surgery. Precise analysis of a set of hip joint images allows an orthopedic surgeon and implant supplier to uniquely match a patient's hip anatomy to an appropriately sized implant and to corresponding surgical cut planes for optimum patient outcomes. Each image of a patient's hip is represented by projections of part or all of an articulated surface joint structure. These projections are ideally provided as a set of thin planar slices formed by magnetic resonance images (MRI) or x-ray computed tomography (CT) images, which may be associated with one or more coronal, axial, and/or sagittal views of the hip joint region. What is needed is a way to properly determine the optimum hip replacement surgery parameters from such images.

In addition to selecting an appropriate hip implant and associated surgical cut planes, for optimum outcomes patient-specific femoral and acetabular jigs are required to aid the surgeon in cutting along the pre-planned cut planes. Therefore, the precise analysis of the hip joint images will allow the implant supplier in consultation with the orthopedic surgeon to construct such patient-specific jigs.

SUMMARY DISCLOSURE

A computer-aided method of pre-operative planning is provided for determining, from patient-specific images of a hip joint, implant sizes and surgical cut planes, and providing both surgical jigs and corresponding hip implant components for a proximal femur and acetabulum. The method includes obtaining a set of coronal, axial and sagittal image slices and along an axis of the femoral neck, marking coordinate positions of selected femur and acetabulum points in the images of the hip anatomy, and performing a best fit analysis to offer a range of suitable implant and cut parameters from those marked image coordinates for selection by a surgeon. After this, the corresponding patient-specific surgical jigs are constructed in accord with the selected implant and cut parameters for the proximal femur and acetabulum.

BRIEF DESCRIPTION OF THE DRAWINGS

FIGS. 13A, 13B and 13C are respective coronal, axial and sagittal views with the identified points A, B and C, the plane OPQR and its normal vector N.

DETAILED DESCRIPTION

MRI Scan Requirements

Figure 1B:
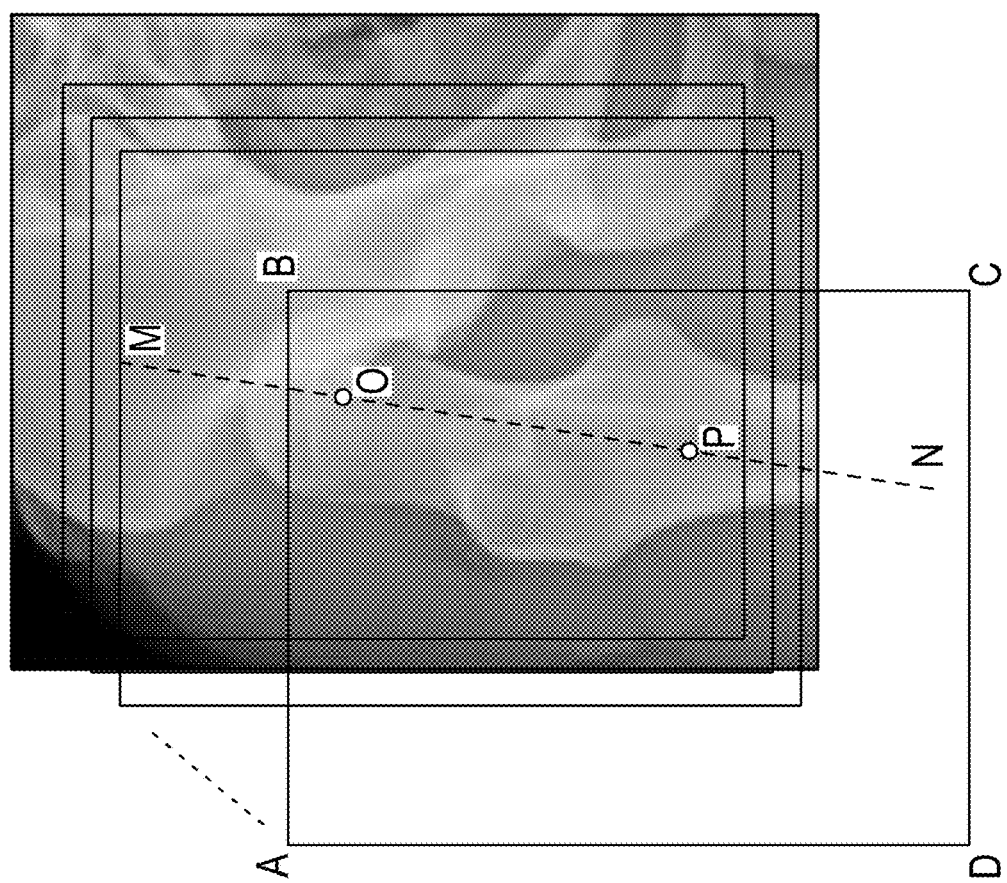
FIGS. 1A, 1B and 1C are respective coronal, sagittal and perspective views of a hip joint with desired image slice planes.
Figure 1A:
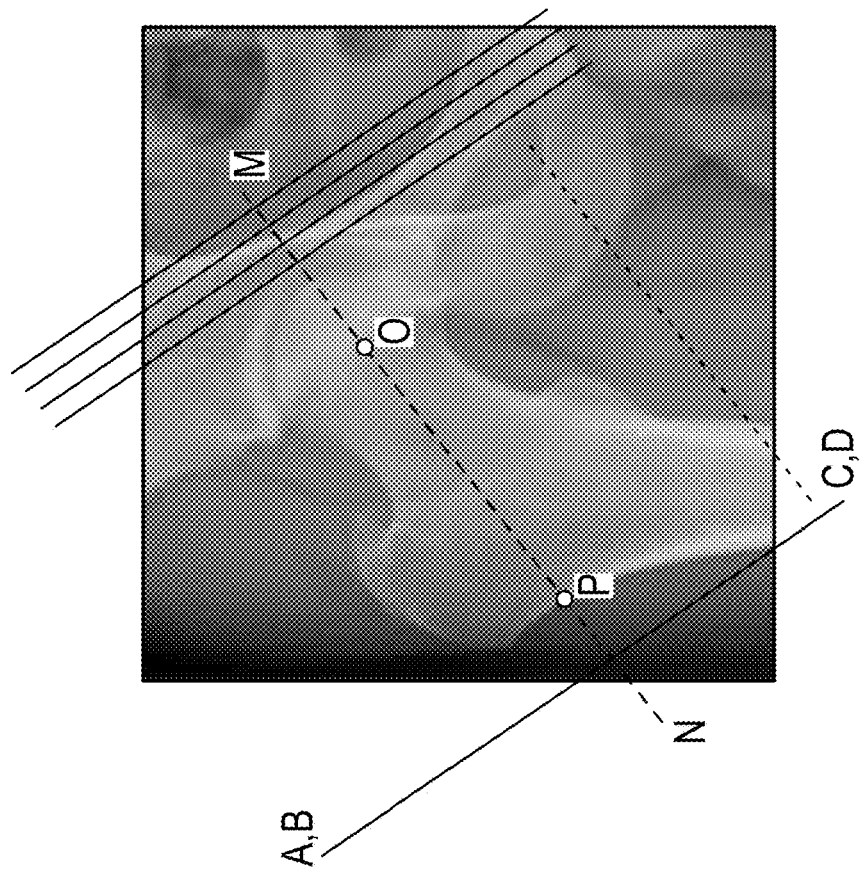
Figure 1C:
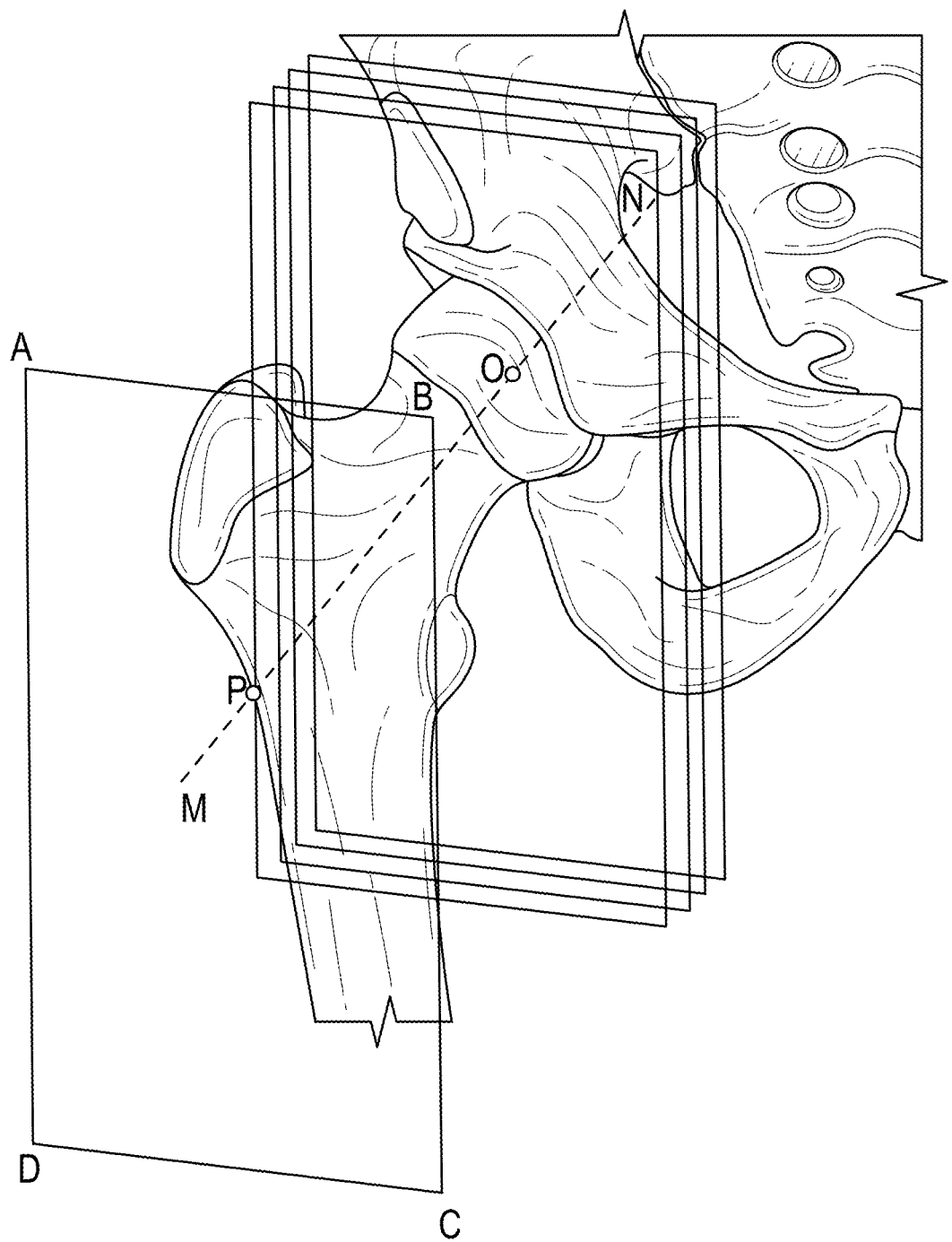

FIG. 1A shows a coronal view of a hip joint in X-ray. Here, the lateral side is to the left and the medial side is to the right. FIG. 1B shows a sagittal view of the hip joint in X-ray. FIG. 1C shows a perspective of the hip joint covering the anatomy of the proximal femur and the acetabulum. In these figures, point O represents the center of the femoral head and point P represents the approximate lateral point around the vastus lateralis at the base of the greater trochanter. A reference line MN, determined connecting points O and P, is used to establish the imaging planes for the series of MRI images to be obtained. MRI image planes ABCD are perpendicular to the reference line OP. The MRI images should include the proximal femur with the femoral head, femoral neck, major and minor trochanter, and the upper portion of femoral shaft.

MRI Check Process

Figure 2A:
FIGS. 2A, 2B and 2C are respective MRI image slices for raw image quality check.
Figure 2B:
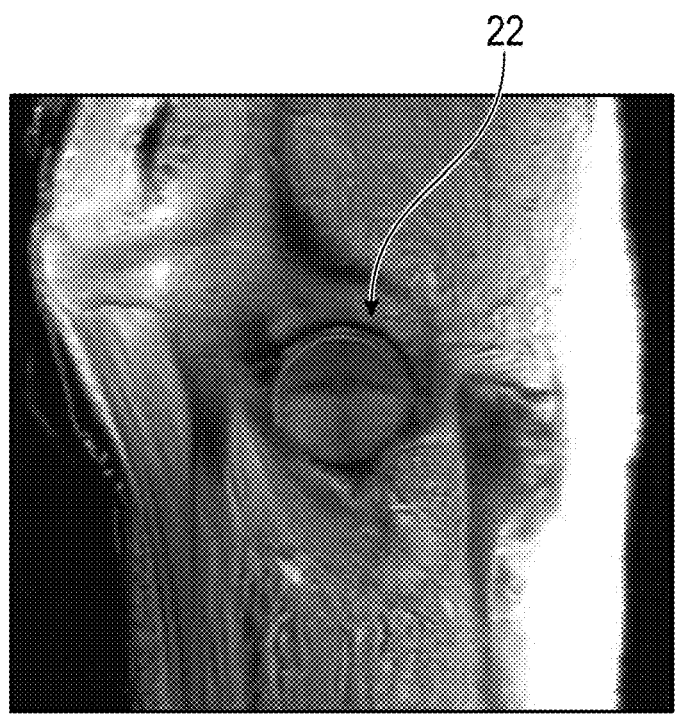
Figure 2C:

FIGS. 2A-2C show the first step of an MRI check procedure. The user checks the quality of MRI raw images starting from the trochanter 21 and femoral shaft, the femoral neck and head 22, to the acetabulum region 23. The image slices must be of sufficient quality to be able to discern anatomical feature boundaries and to establish position coordinates of the anatomical features. If not, new MRI images will need to be obtained.

Figure 3:
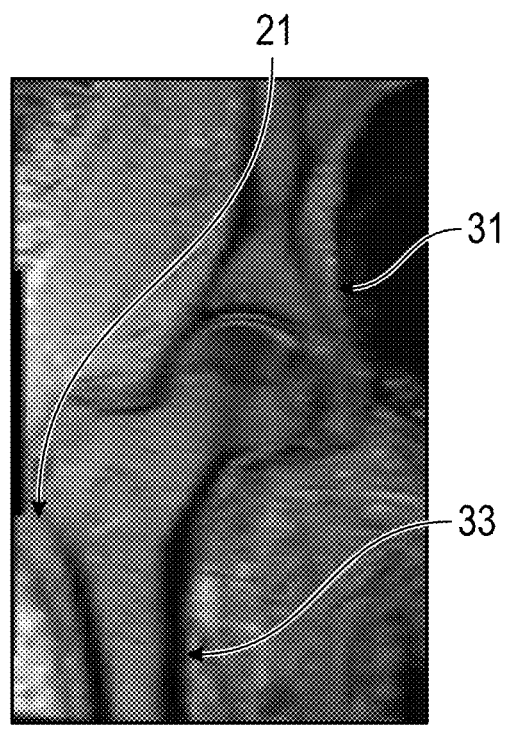
FIG. 3 is a coronal image of a hip joint region for checking the scope of the image.

FIG. 3 shows a coronal view of a hip joint region. The second step of the image checking process is for the user to check if the images fully include the bottom of the acetabulum 31, the lateral of the major trochanter 21 and the proximal femoral shaft 33. If not, new MRI images will need to be obtained.

Figure 4:
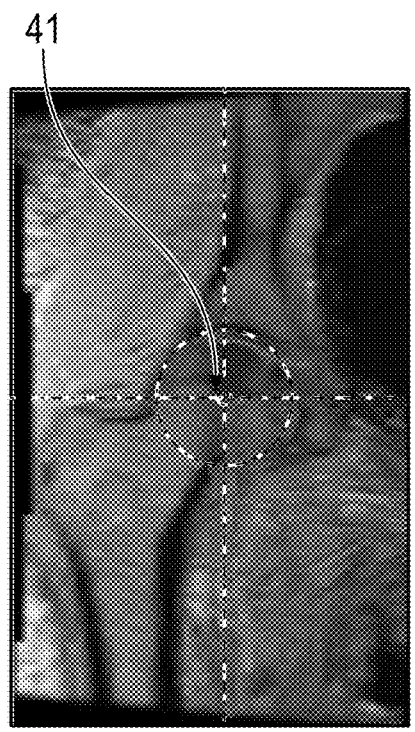
FIG. 4 is a coronal image of the hip joint region with identification of the femoral head and its center point.

The third and last step of the MRI check process is to approximately identify the center of the femoral head 41 using circle icons, as shown in FIG. 4. The approximate center point will be used as an initial center point of the next process, FEMUR PLANNING 1. If the perimeter outline of the femoral head cannot be discerned sufficiently to place a circle icon over the image, then new MRI images will be needed.

Femur Planning 1

Figure 5A:
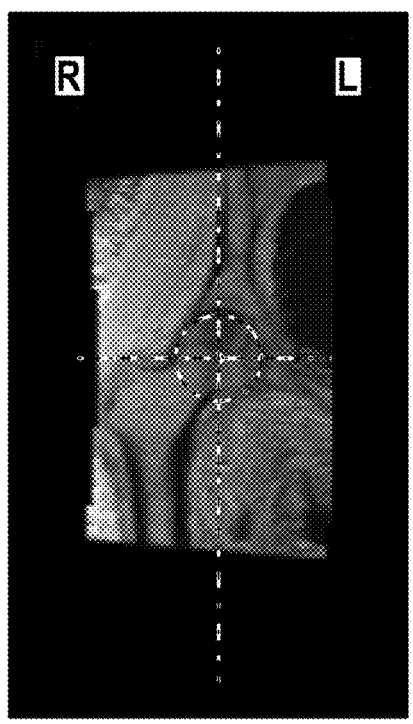
FIGS. 5A, 5B and 5C are respective coronal, axial and sagittal views showing the identified femoral head and center point.
Figure 5B:
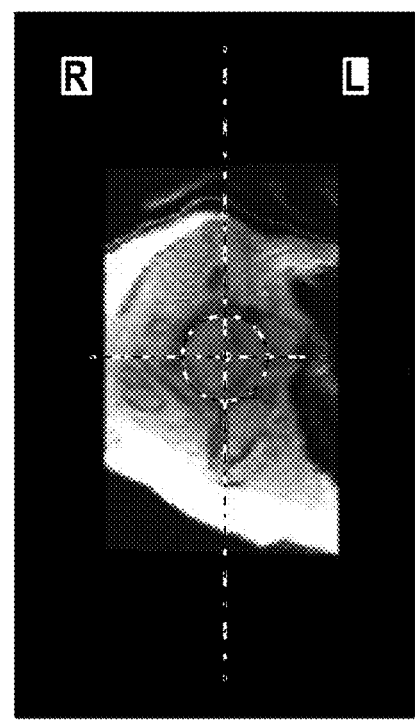
Figure 5C:
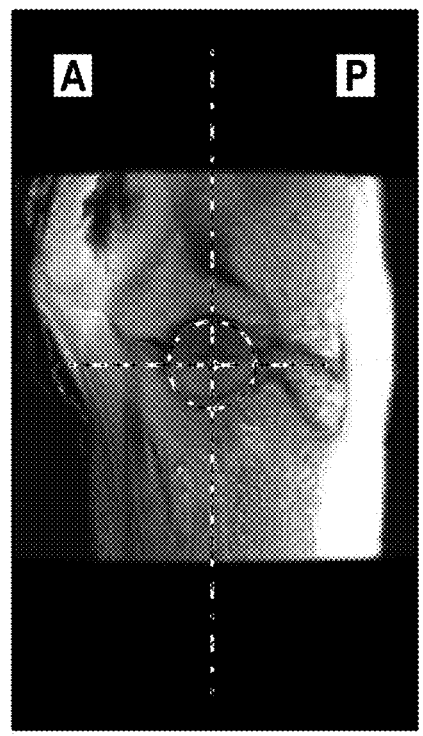

The first step of femur planning 1 is to precisely identify the center of the femoral head using all coronal, axial, and sagittal views. The circle icon is positioned at the point defined in step three of the previous MRICHECK process. The circle icon can be moved translationally, and its diameter can be adjusted by dragging a computer mouse until it precisely overlays the perimeter of the femoral head in each image orientation, as shown in FIGS. 5A-5C in the respective coronal, axial and sagittal views. R-L indicate the right and left sides of the anatomy, while A-P indicate the anterior and posterior sides of the anatomy.

Figure 6A:
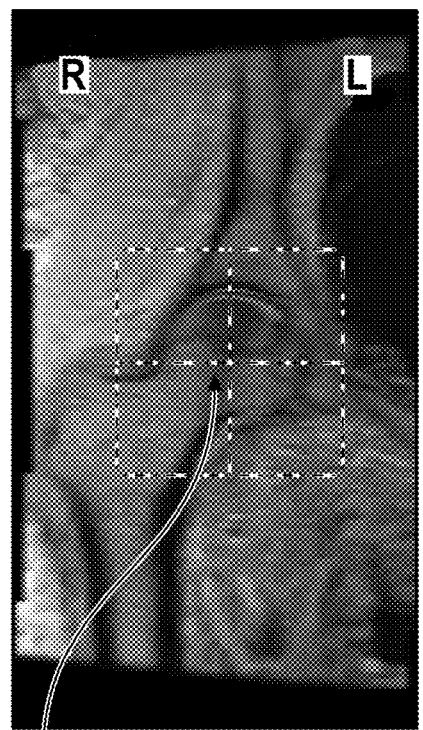
FIGS. 6A, 6B and 6C are respective close-up coronal, axial and sagittal views with cross/rectangle icons aligned with the center of the femoral head.
Figure 6B:
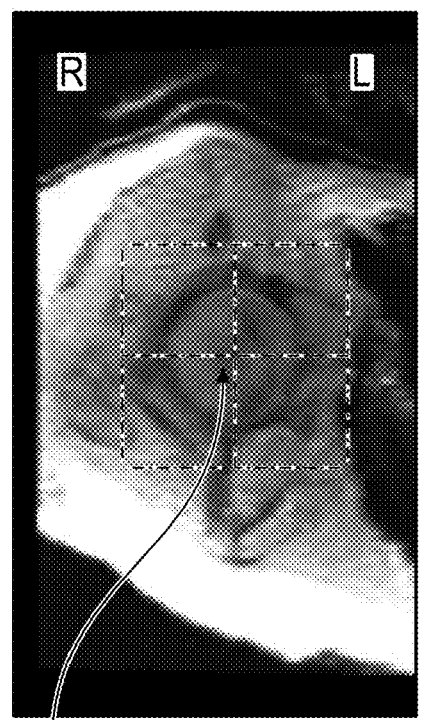
Figure 6C:
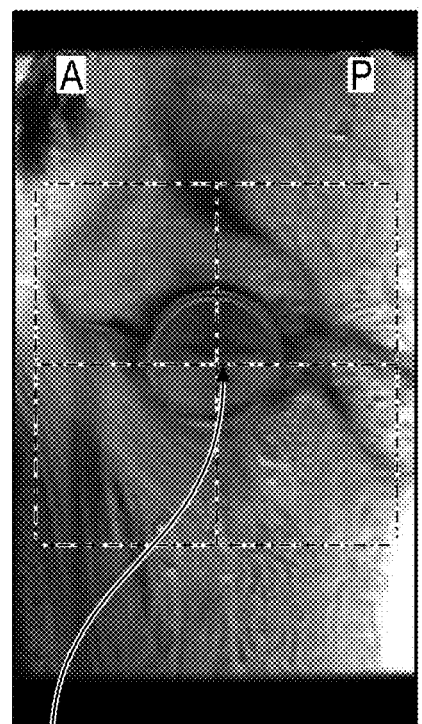

The next step is to align the proximal femur using cross/rectangle as shown in FIGS. 6A-6C in respective coronal, axial and sagittal views. The center of each cross/rectangle icon represents the center 41 of the femoral head, as previously established using the circle icon. The crosses represent coordinate axes with the femoral head center 41 as origin.

Figure 7:
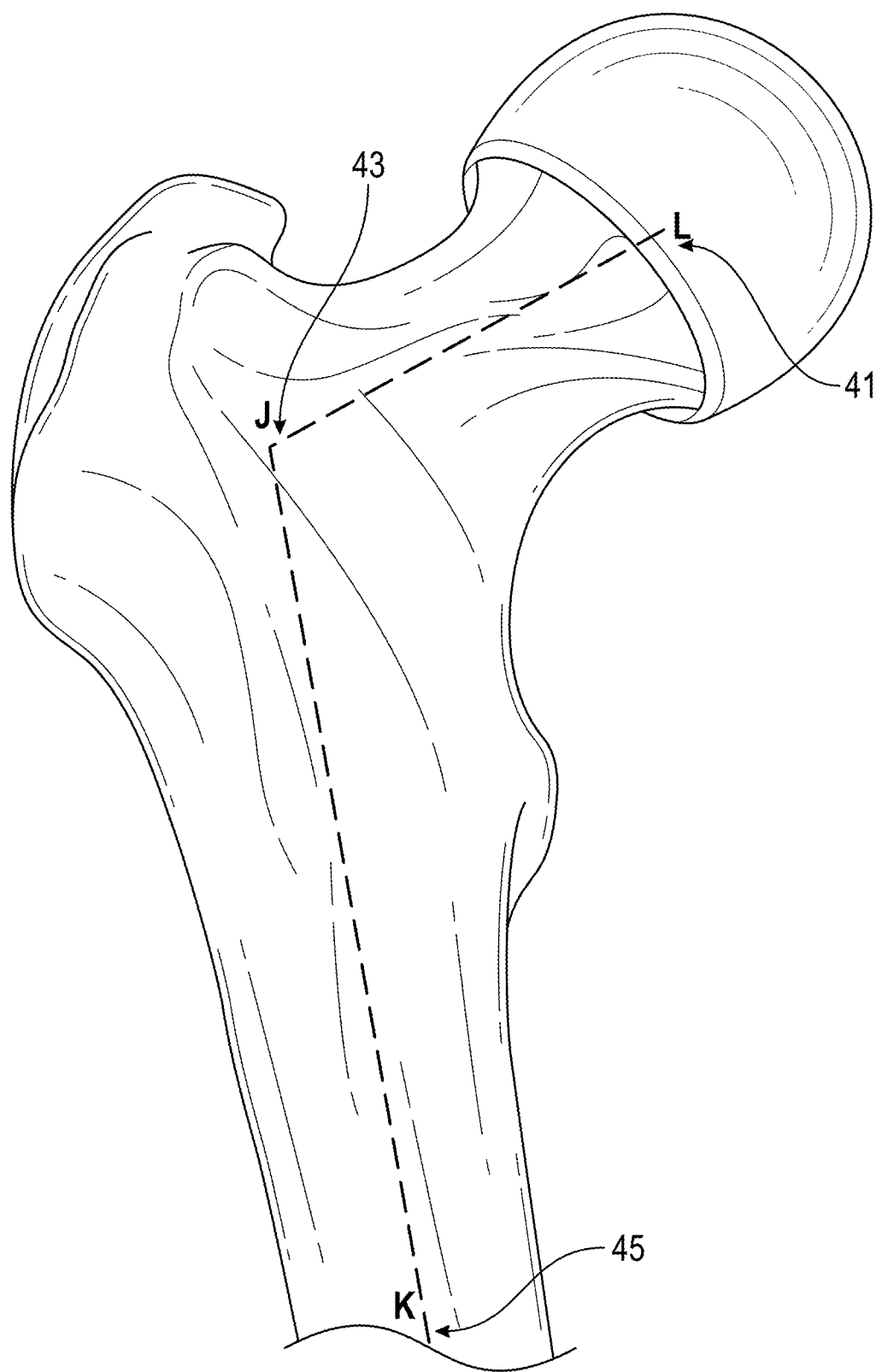
FIG. 7 is a perspective view of the proximal femur region illustrating three alignment points: center of femoral head, major trochanter point, and midpoint of femoral shaft.

FIG. 7 shows the alignment requirements. Point J is defined as the midpoint 43 of the major trochanter in axial view down to point K at a midpoint 45 along the proximal femoral shaft. The line JK is then defined as the femoral shaft reference line. The point L represents the center 41 of the femoral head. Point J is again the midpoint 43 of the major trochanter in sagittal view. Line JL then represents the femoral neck reference line.

Figure 8A:
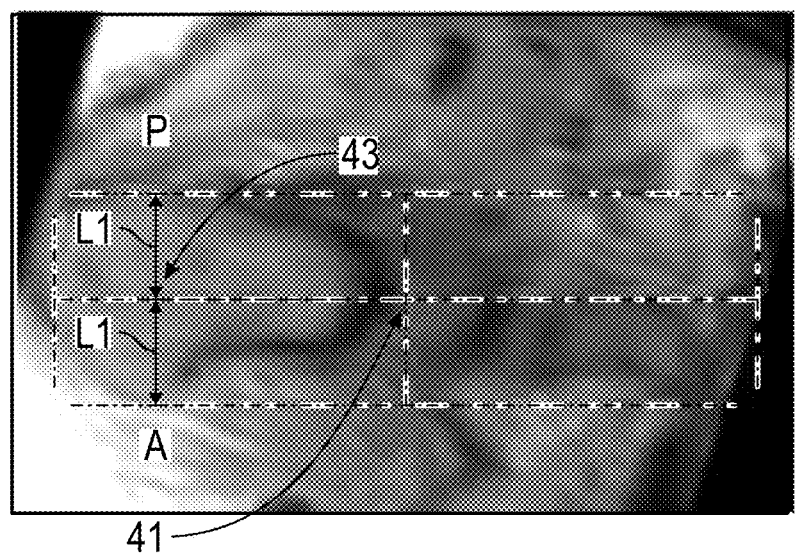
FIGS. 8A and 8B are respective axial and sagittal views showing identification of the major trochanter point.
Figure 8B:
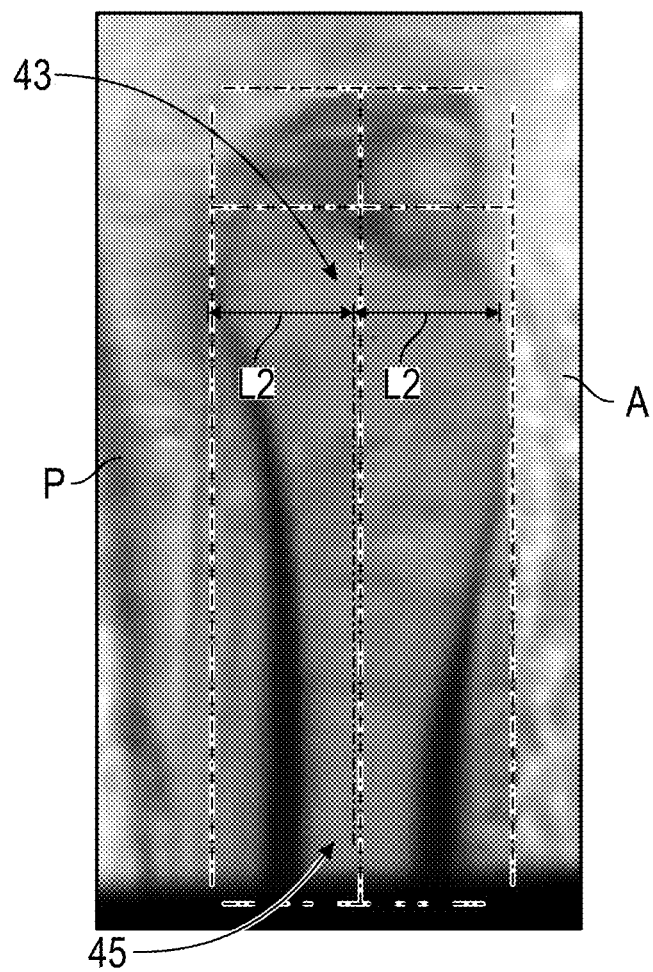

FIGS. 8A and 8B show the identification of the mid-trochanter point (J) around the major trochanter region in respective axial and sagittal views, where A and P designate the anterior and posterior sides of the anatomy. Cross/rectangle icons display equal distances of L1 in coronal view and L2 in sagittal view to the furthest anterior and posterior extent of the femur.

Figure 9A:
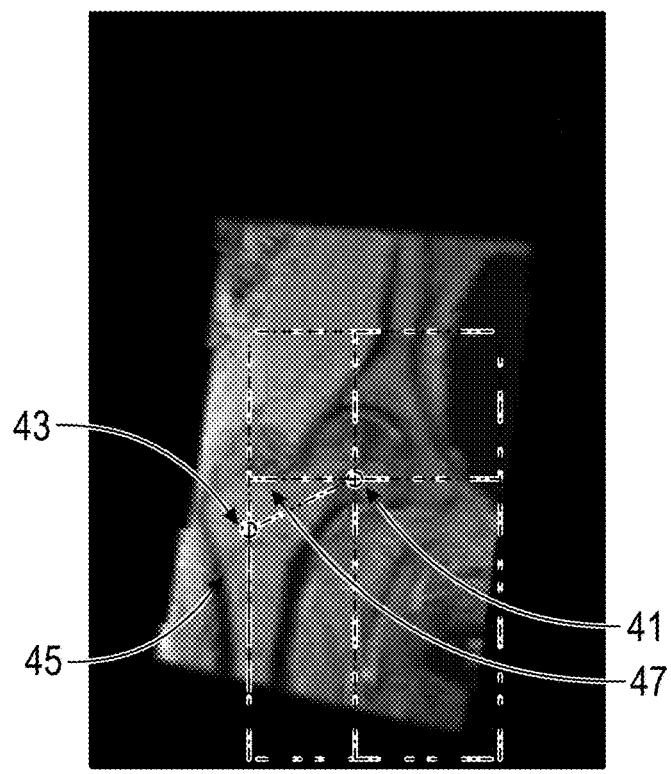
FIGS. 9A, 9B and 9C are respective coronal, axial, and sagittal views showing initial planned implant alignment along the femoral shaft from the center of the femoral head to the major trochanter point.
Figure 9B:
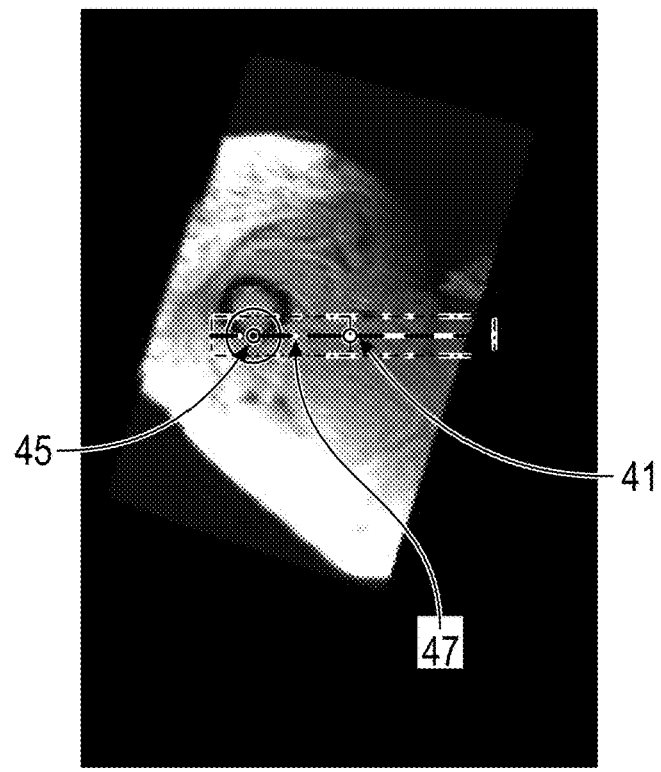
Figure 9C:
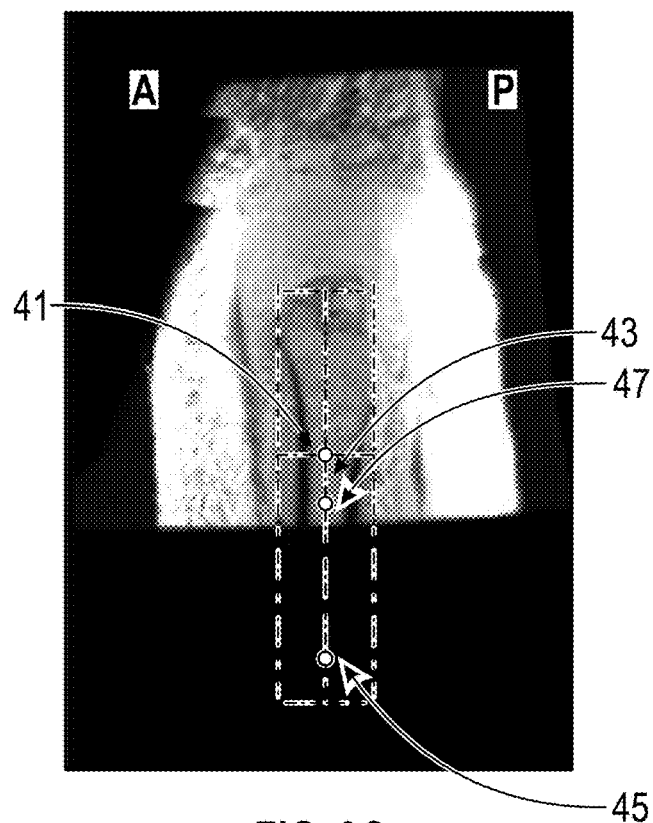

FIGS. 9A-9C show the alignment of the proximal femur in coronal, axial and sagittal views for the initial placement of an implant by simultaneously rotating cross/rectangle icons with respect to the center 41 of the femoral head in each view. In the coronal view (FIG. 9A), the femoral shaft reference line 47 starts from the mid-trochanter point 43 to the center point 45 of the femoral shaft. In the axial view (FIG. 9B), the femoral neck reference line starts at the center 41 of the femoral head to the center 45 of the femoral shaft. As seen in the sagittal view (FIG. 9C), both the femoral neck reference and the femoral shaft reference lines coincide with each other starting from the center 41 of the femoral head, to the mid-trochanter point 43, and finally to the center 45 of the femoral shaft.

Acetabulum Planning 1

Figure 10:
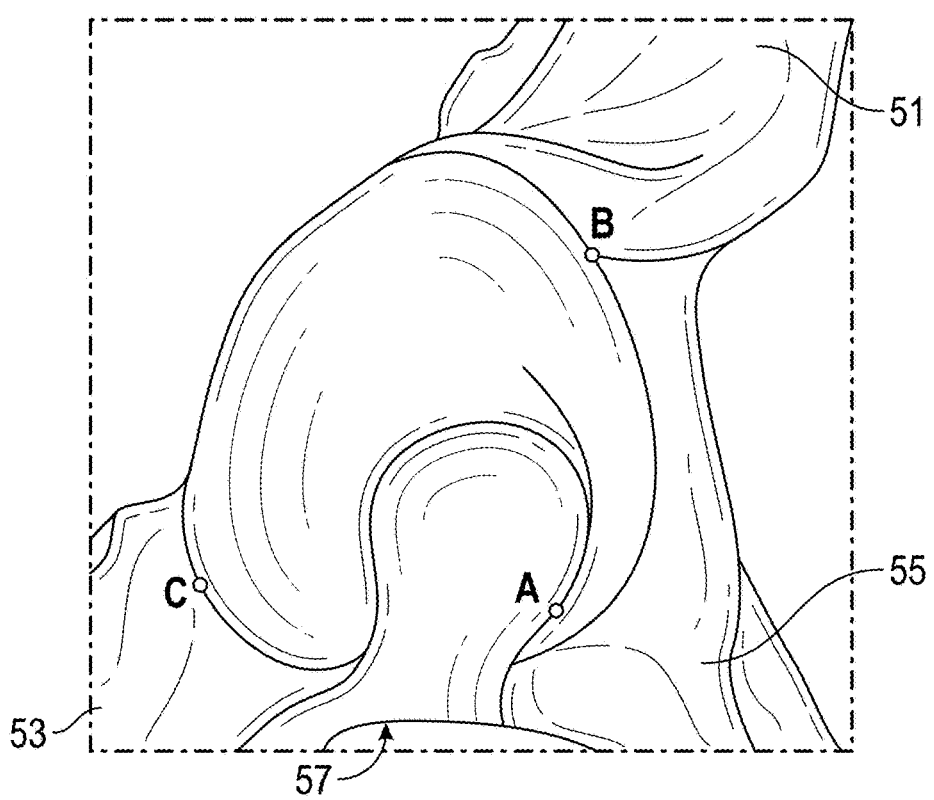
FIG. 10 is a perspective view of the acetabulum anatomy of a hip with three identified points A, B, and C on the pubis, ilium, and ischium.

FIG. 10 shows the anatomy of the acetabulum. The horn tips near the acetabular notch 57 are indicated by the letters A and C. Point A is on the pubis 55, while point C is on the ischium 53. Along the rim, two inflexions can be systematically identified: point B on the ilium 51 represents the most cranial inflexion where the indentation of the anterior part of the rim appears; point C, the most caudal inflexion, was placed at the beginning of the curvature of the posterior horn. Points B and C allow the division of the rim into two parts named the anterior and posterior acetabular rims.

Figure 11:
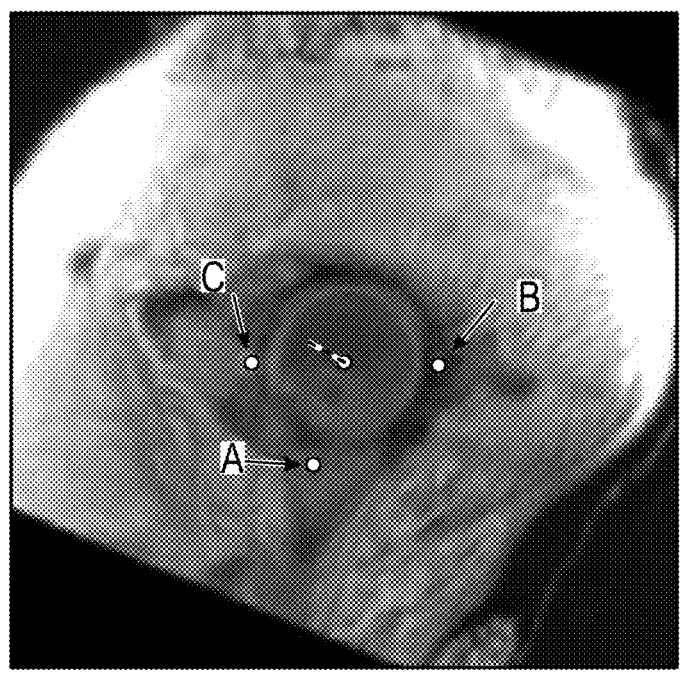
FIG. 11 is a sagittal MRI view of the acetabulum with the three identified points.

FIG. 11 shows the identification of Points A, B and C from the sagittal view of MRI images.

Figure 12:
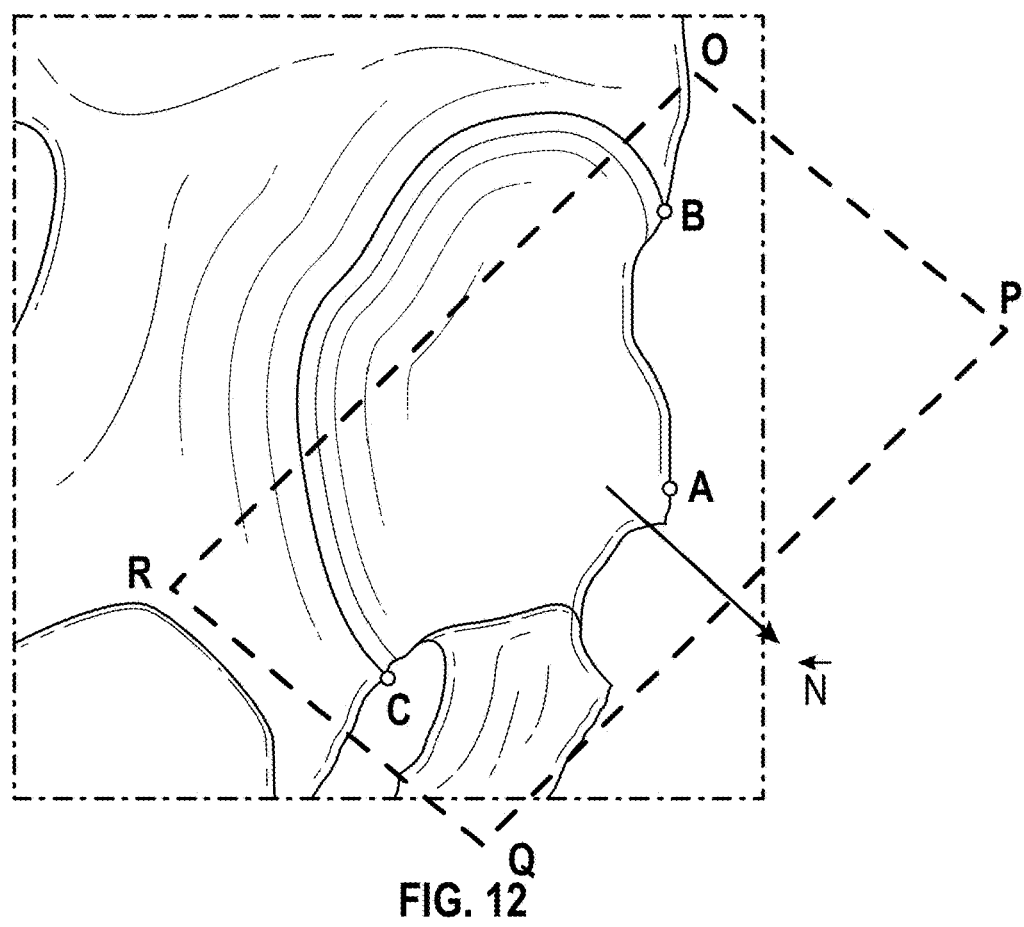
FIG. 12 is a perspective view of the acetabulum anatomy showing a plane OPQR on which the identified points A, B, and C all lie.

FIG. 12 shows that the plane OPQR is found where the Points A, B and C lie. The vector N is perpendicular to the plane OPQR. The planning tool then rotates the MRI images perpendicular to the plane OPQR using the vector N.

FIGS. 13A-13C show the alignment of the acetabulum of MRI images after rotation with respect to vector N. These three points A, B and C will used for placement of the acetabulum implant and fixation points of the acetabulum jig are used in reference to the three points A, B and C where there is enough volume of bone material for the placement of pins.

Figure 14:
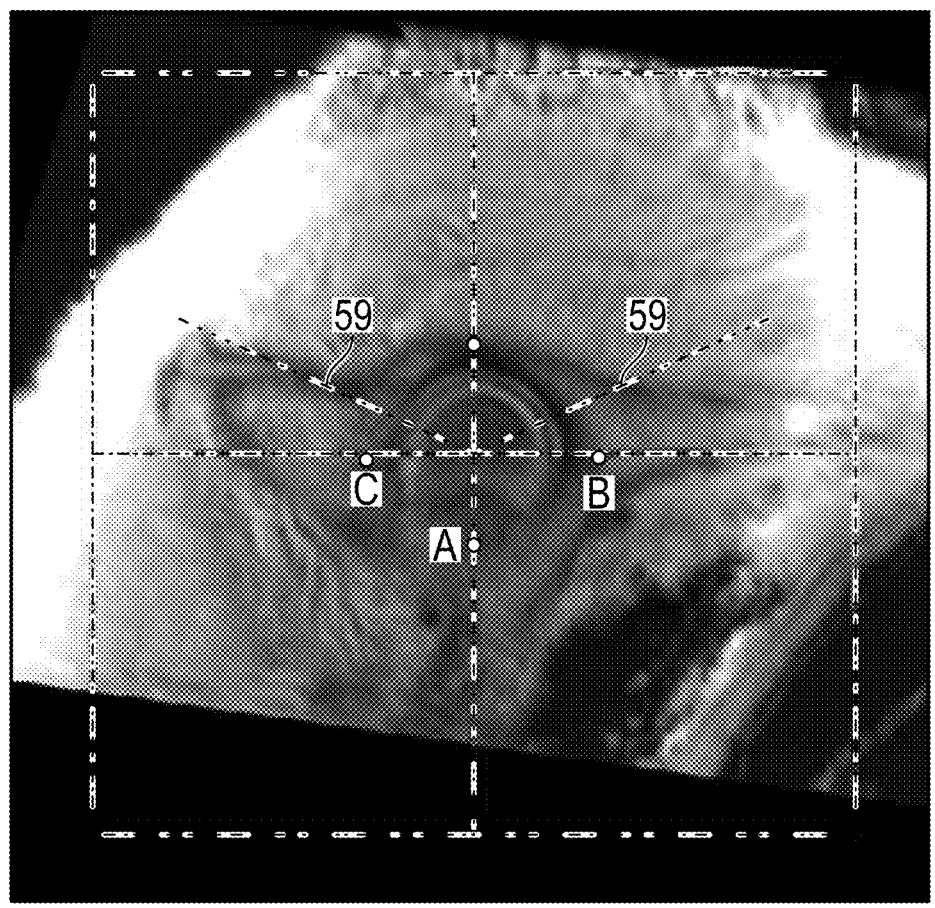
FIG. 14 is a sagittal view of the acetabulum in plane OPQR with the ilio-ischiatique midpoint shown.

FIG. 14 shows the additional rotation in sagittal view. Using CROSS/RECTANGLE icon, the sagittal view is rotated along the point A and approximate mid-point of ilio-ischiatique 59.

Femur Planning 2

Figure 15A:
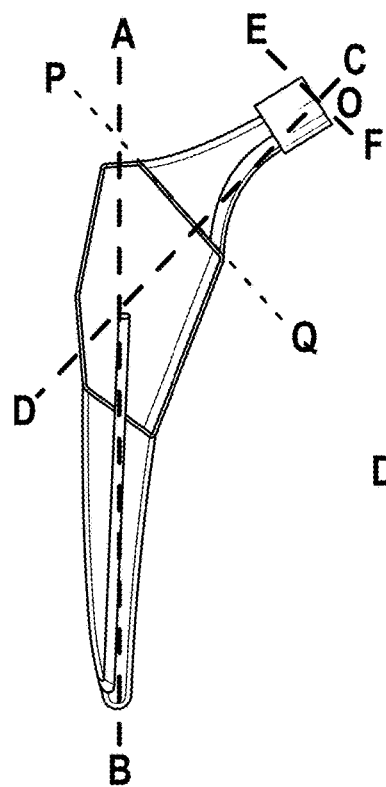
FIGS. 15A, 15B and 15C are side plan views of respective standard, mini, and short stem hip implants for the femur.
Figure 15B:
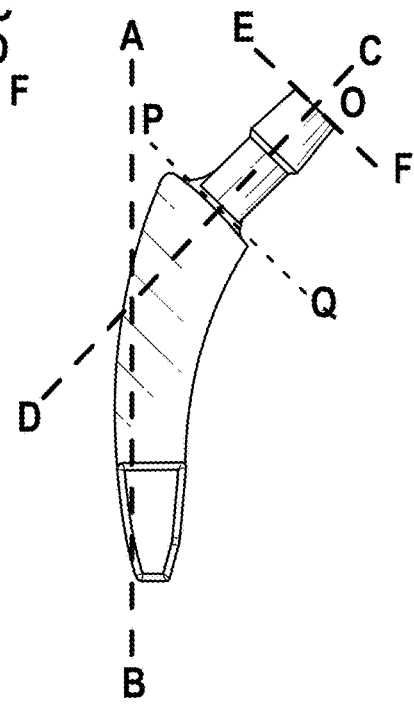
Figure 15C:
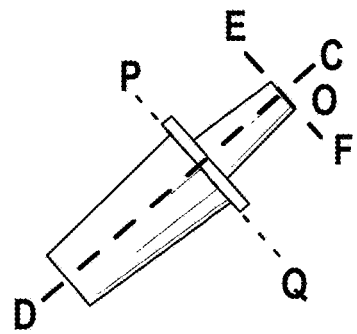

FIG. 15A shows a standard femoral hip implant, FIG. 15B is a mini hip implant and FIG. 15C shows a short stem hip implant. Line PQ represents a femoral cut plane for the standard, mini and short stem hip implant. Line CD represents the line perpendicular to the cut plane line PQ. The intersection of lines EF and CD represent the center O of the femoral head. The line AB represents the line from mid-trochanter point to the center of the proximal femur center.

Figure 16A:
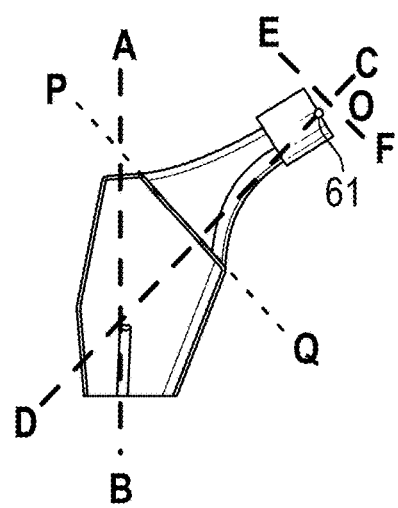
FIGS. 16A and 16B are closeup side plan views of the standard femoral implant component with shown with associated parameter points and lines.
Figure 16B:
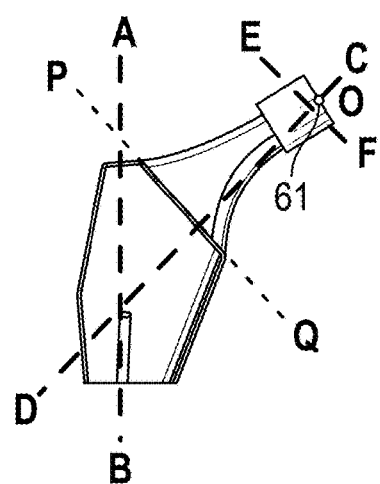
Figure 17A:
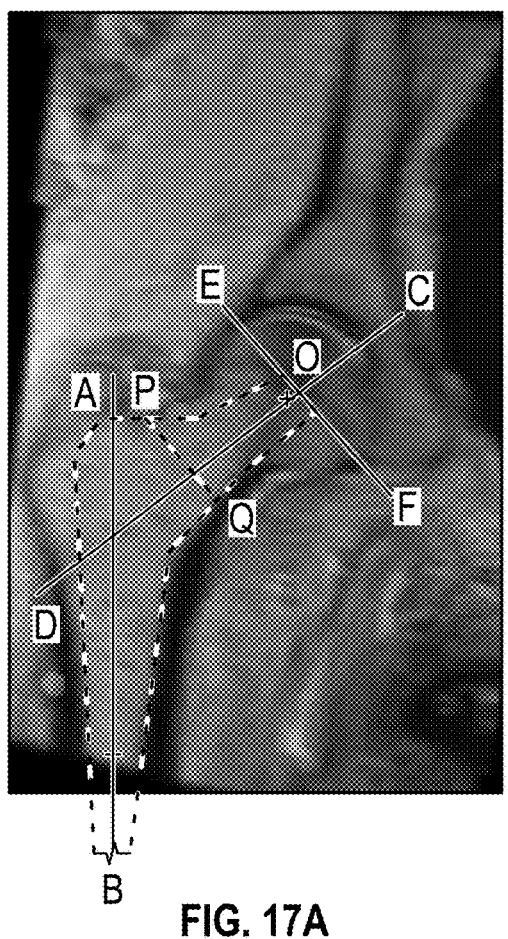
FIGS. 17A-17E show the outline of a standard femoral hip implant component overlaid over respective coronal (17A), axial (17B-17D, translated along the line CD) and sagittal (17E) views.
Figure 17B:
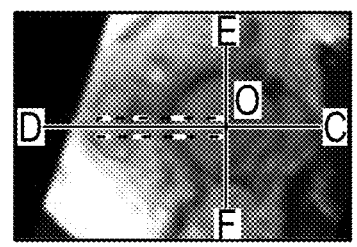
Figure 17C:
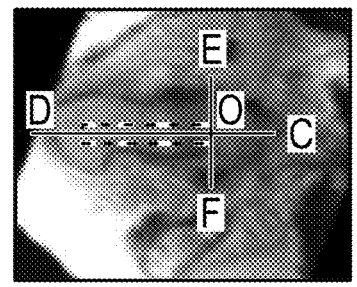
Figure 17D:
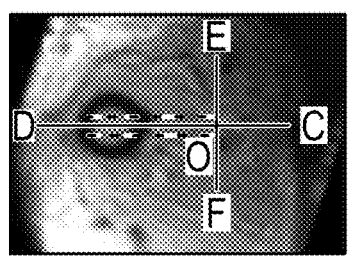
Figure 17E:
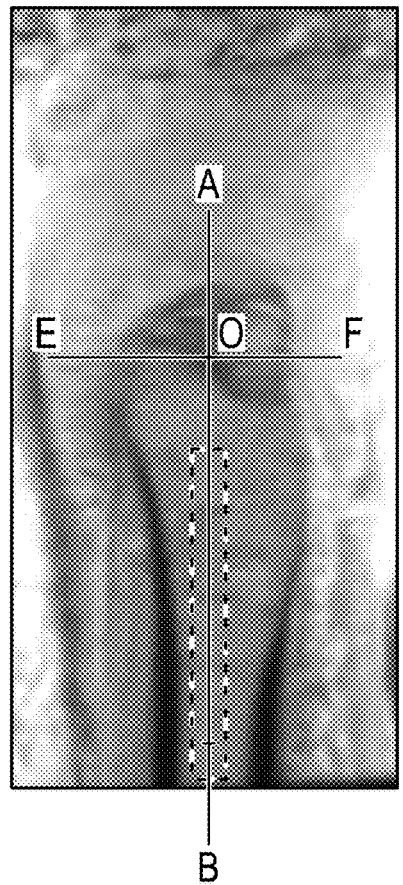
Figure 18A:
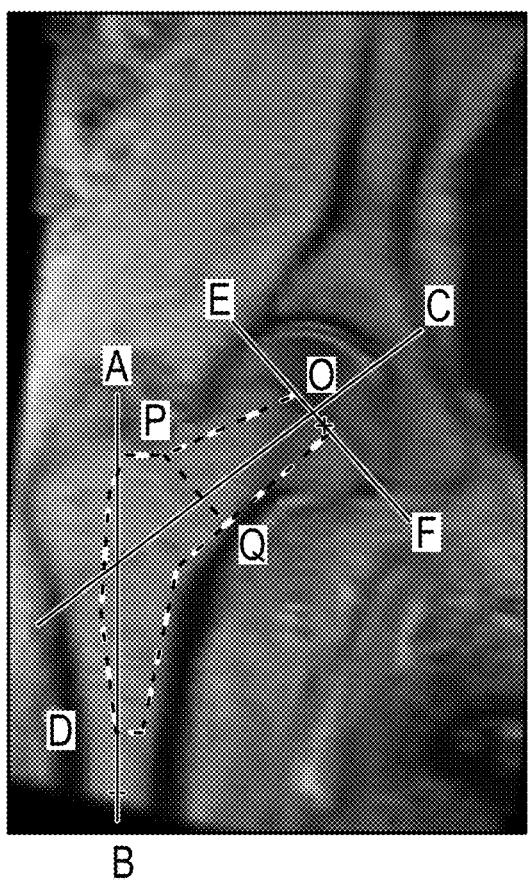
FIGS. 18A-18E show the outline of a mini femoral hip implant component overlaid over the same coronal, axial and sagittal views as FIGS. 17A-17E.
Figure 18B:
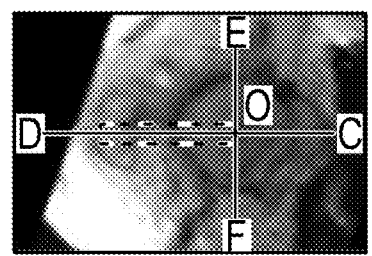
Figure 18C:
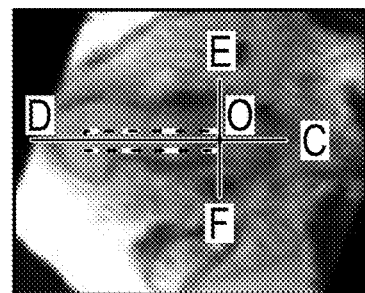
Figure 18D:
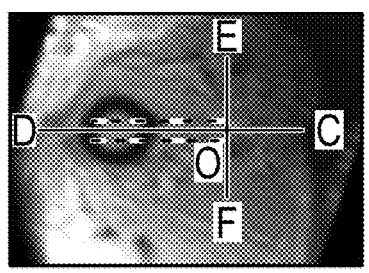
Figure 18E:
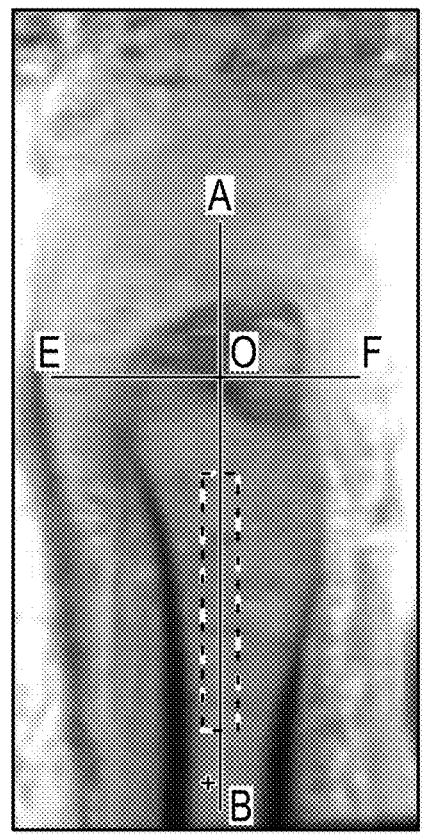
Figure 19A:
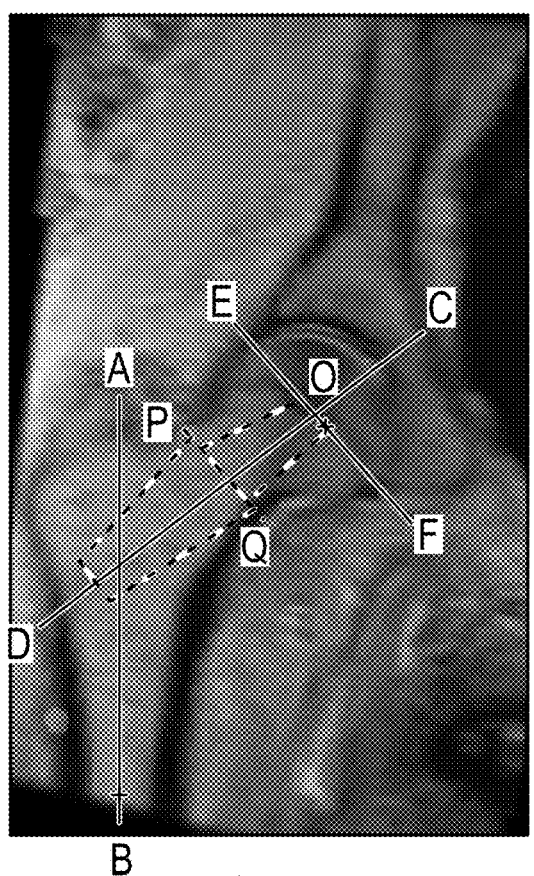
FIGS. 19A-19E show the outline of a short stem femoral hip implant component overlaid over the same coronal, axial and sagittal views as FIGS. 17A-17E.
Figure 19B:
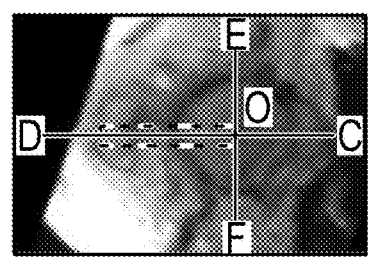
Figure 19C:
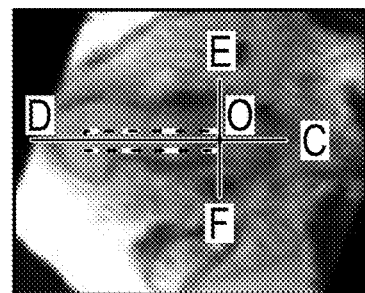
Figure 19D:
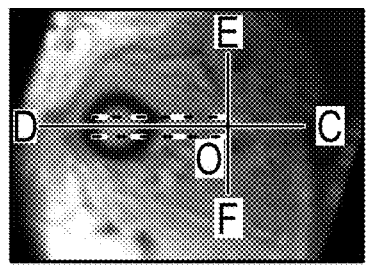
Figure 19E:
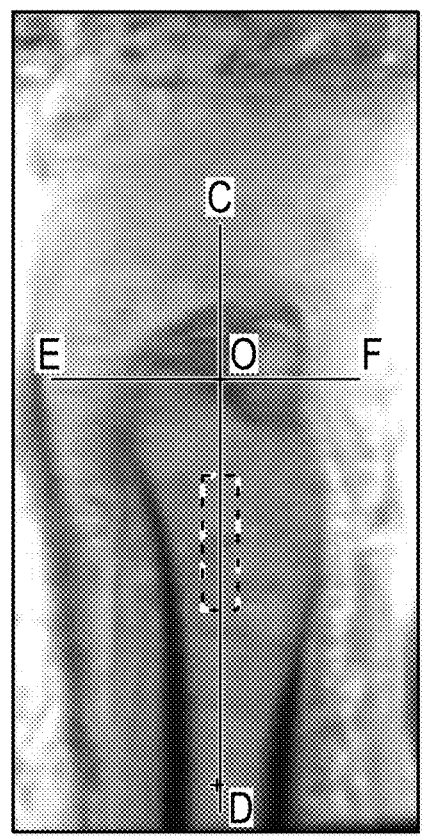

FIGS. 16A and 16B show that the femoral hip implant center O translates along line CD where the anatomical center of the femoral head 61 is stationary.

FIGS. 17A-17E show the outline of a standard femoral hip component superimposed on MRI images. The overlaid outline can be used to select the implant size based on the coronal, axial and sagittal MRI views. The component can be translated along the line CD and line AB and can be rotated with respect to the femoral head center O.

FIGS. 18A-18E show that superimposing an outline of a mini femoral hip component on MRI images can be used to select the implant size based on the coronal, axial and sagittal MRI views. The overlaid component can be translated along the line CD and line AB and can be rotated with respect to the femoral head center O.

FIGS. 19A-19E show that superimposing an outline of a short stem implant on MRI images can be used to select the implant size based on the coronal, axial and sagittal MRI views. The overlaid component can be translated along the line CD and can be rotated with respect to the femoral head center O.

Figure 20:
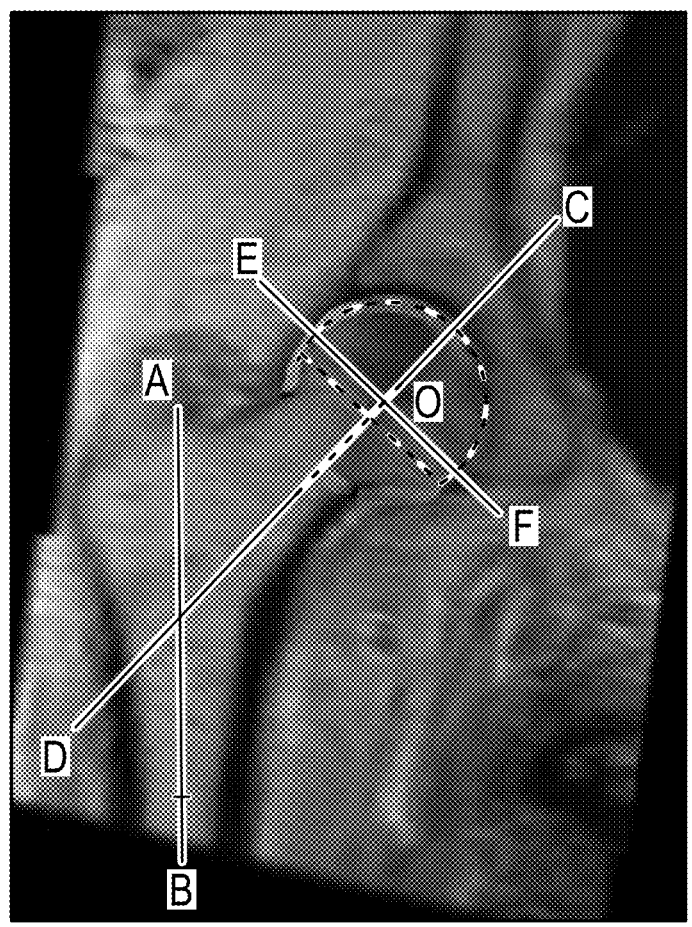
FIG. 20 shows a coronal view of a resurfacing femoral hip implant component superimposed on an MRI image.

Furthermore, using the mini femoral hip component approach, FIG. 20 shows that superimposing an outline of a resurfacing implant on MRI images can be used to select the implant size based on the coronal, axial and sagittal MRI views. The overlaid component can be translated along the line CD and can be rotated with respect to the femoral head center O.

Acetabulum Planning 2

Figure 21A:
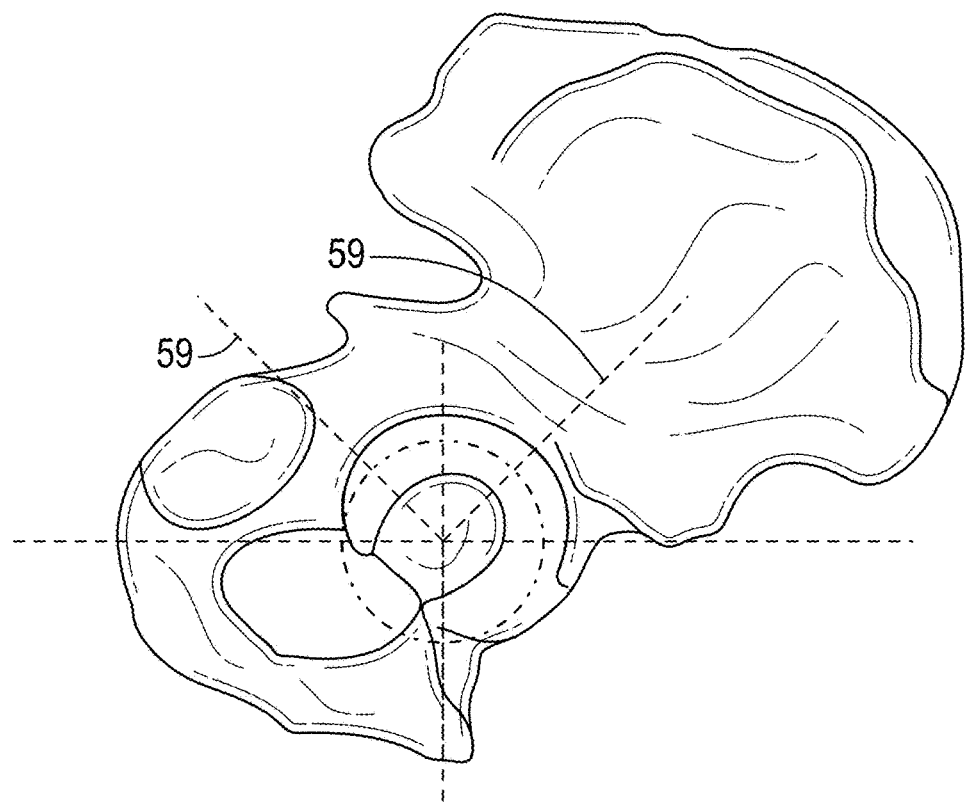
FIG. 21A is a plan view of the acetabulum oriented according to the direction of the femoral shaft.
Figure 21B:
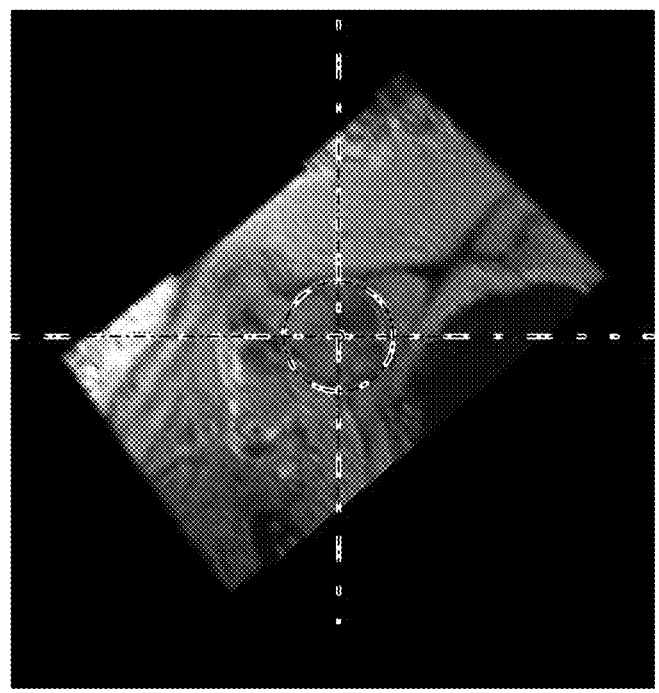
FIGS. 21B, 21C and 21D are respective coronal, axial and sagittal MRI image views identifying the center of the acetabulum cup.
Figure 21C:
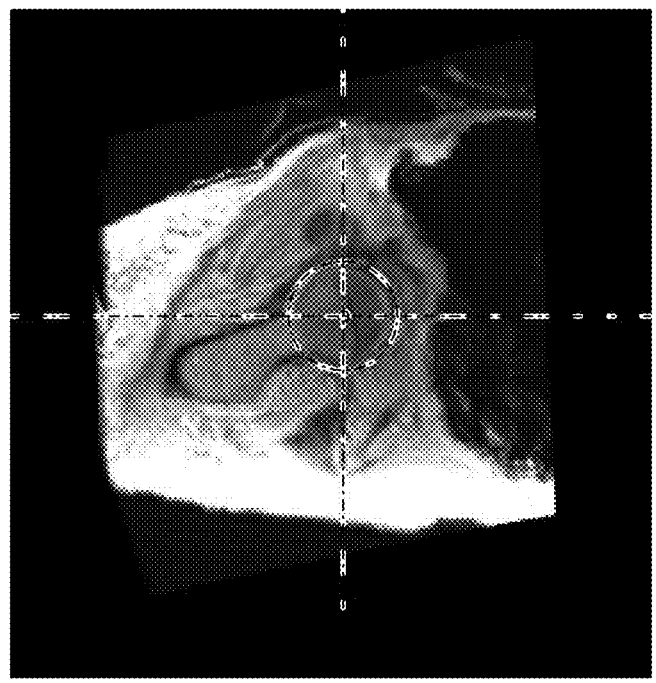
Figure 21D:
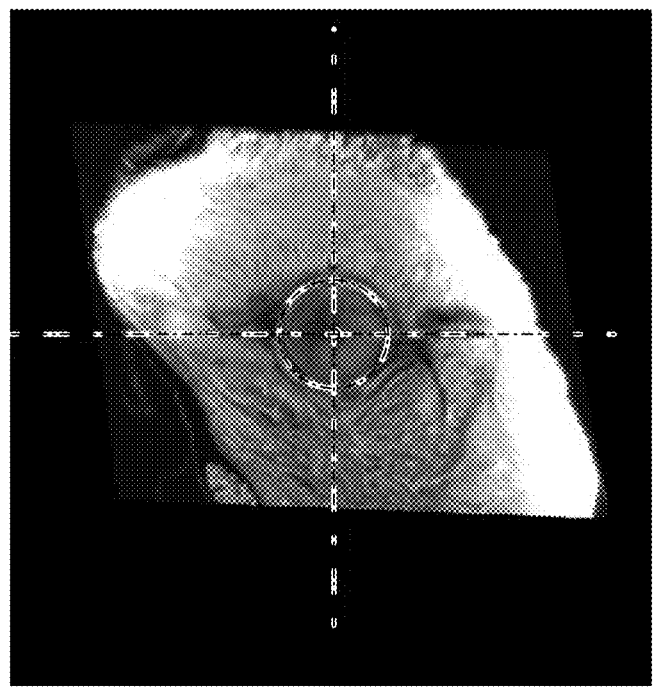

FIG. 21A shows the orientation of the acetabulum, which was planned in the PLANNING 1 process, where the lines 59 indicate the ilio-ischiatique lines. FIGS. 21B-21D show identifying the center of the acetabulum cup by means of a circle overlay of the coronal, axial and sagittal views of MRI images in the orientation shown in FIG. 21A.

Figure 22A:
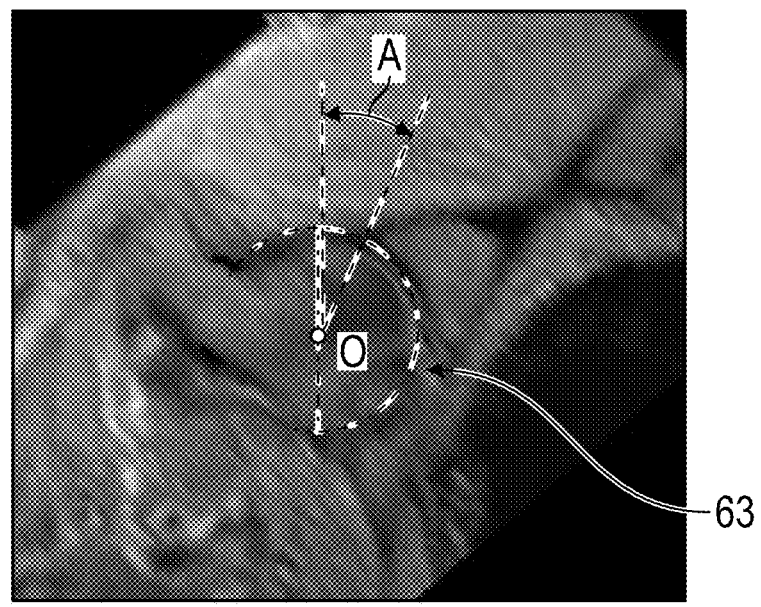
FIGS. 22A and 22B are images showing the planned position and sizing of the acetabulum cup implant.
Figure 22B:
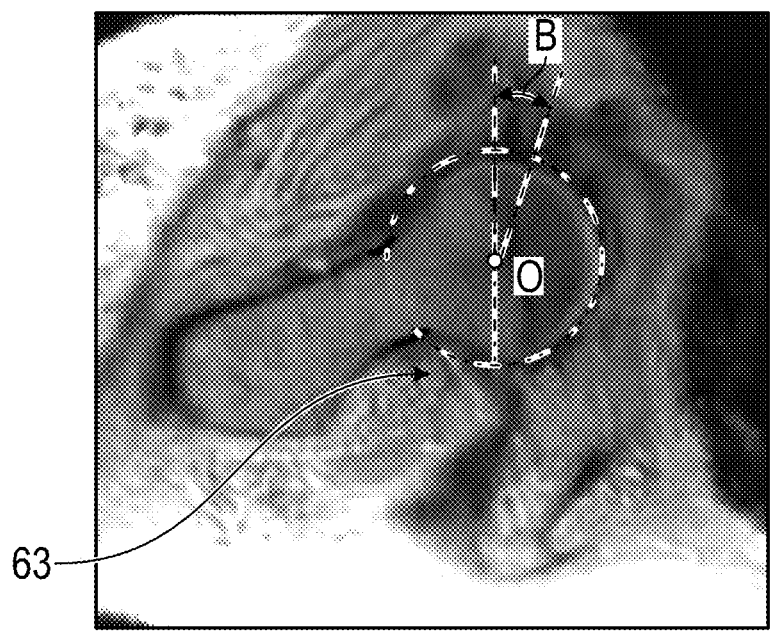

FIGS. 22A and 22B show the position and sizing of acetabulum cup implant 63. The implant rotates with respect to the center O to adjust the position with angles A and B.

Femur Jig Design

Figure 23A:
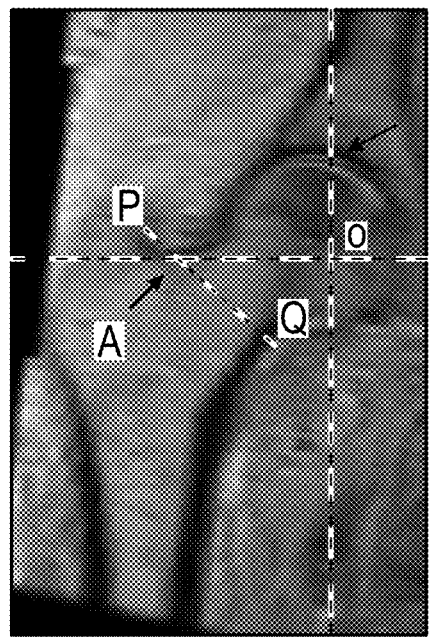
FIGS. 23A and 23B show rotation of the coronal view of hip joint region so that a proposed femoral cut plane PQ is vertical.
Figure 23B:
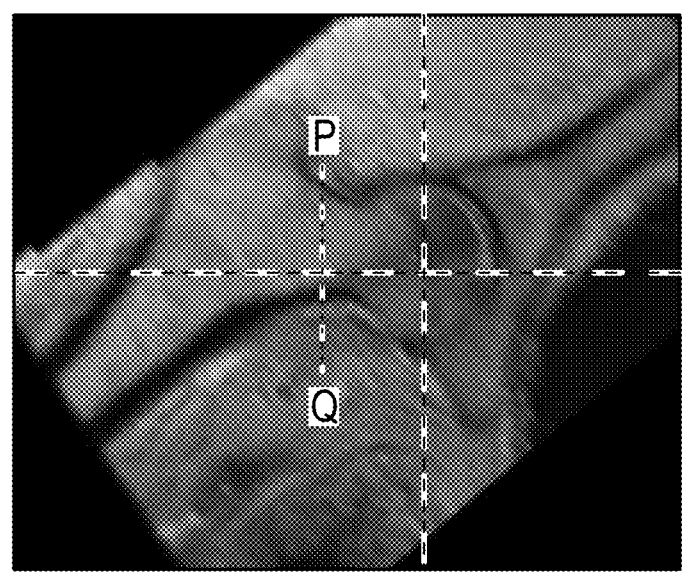

FIGS. 23A and 23B show the rotation of coronal view with an angle A between the cut plane line PQ and vertical line. The rotation gives the coronal view Line PQ parallel to vertical Line.

Figure 24A:
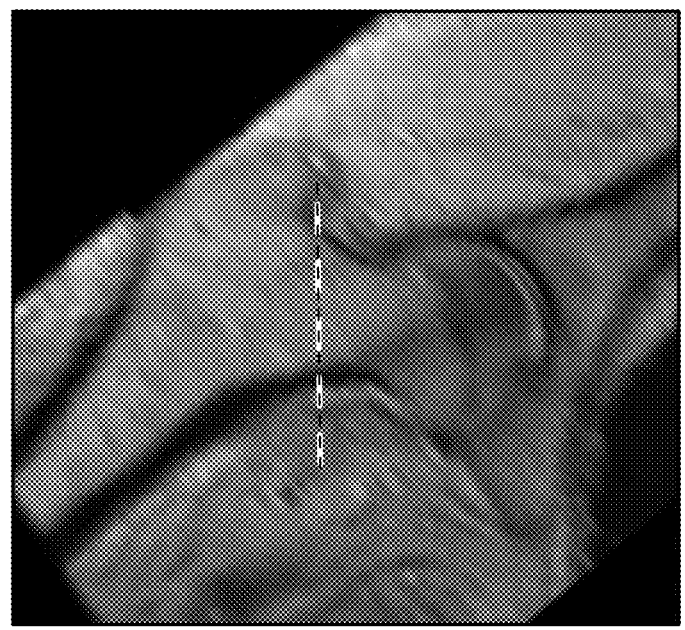
FIGS. 24A and 24B are respective coronal and sagittal views showing first segmentation splines at the bottom of the major trochanter.
Figure 24B:
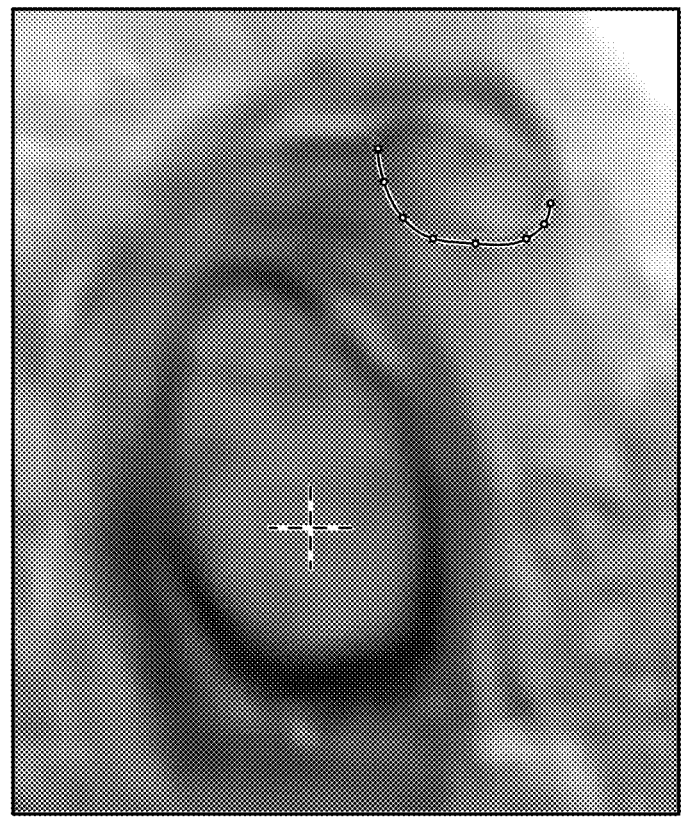
Figure 25A:
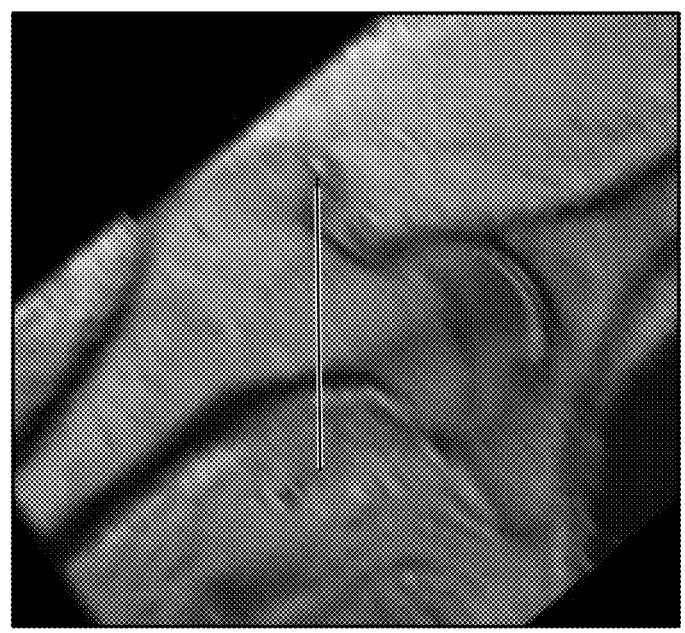
FIGS. 25A, 25B and 25C are respective coronal, posterior sagittal and anterior sagittal views showing second segmentation splines at the root of the femoral neck.
Figure 25C:
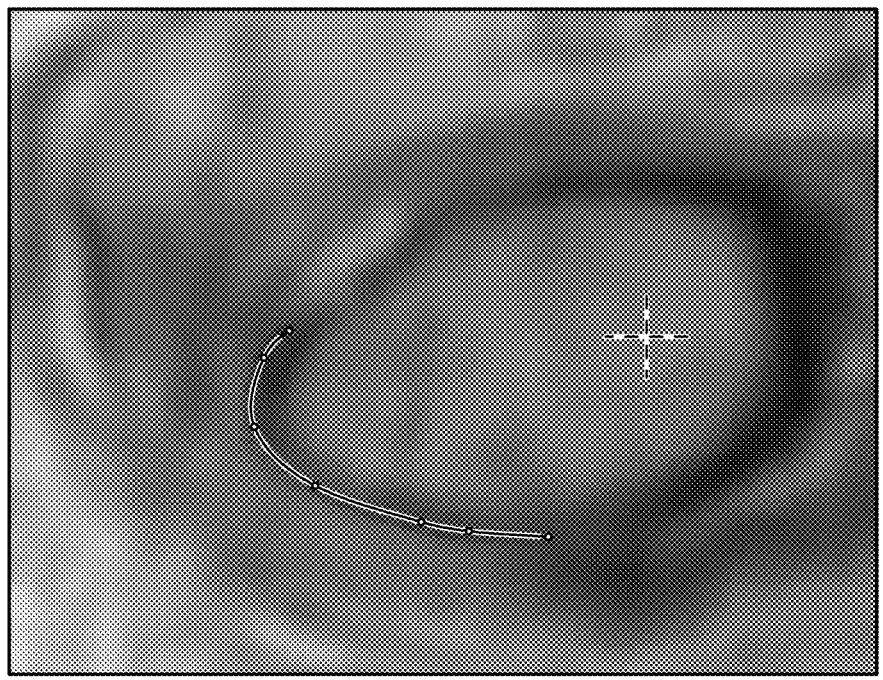
Figure 25B:
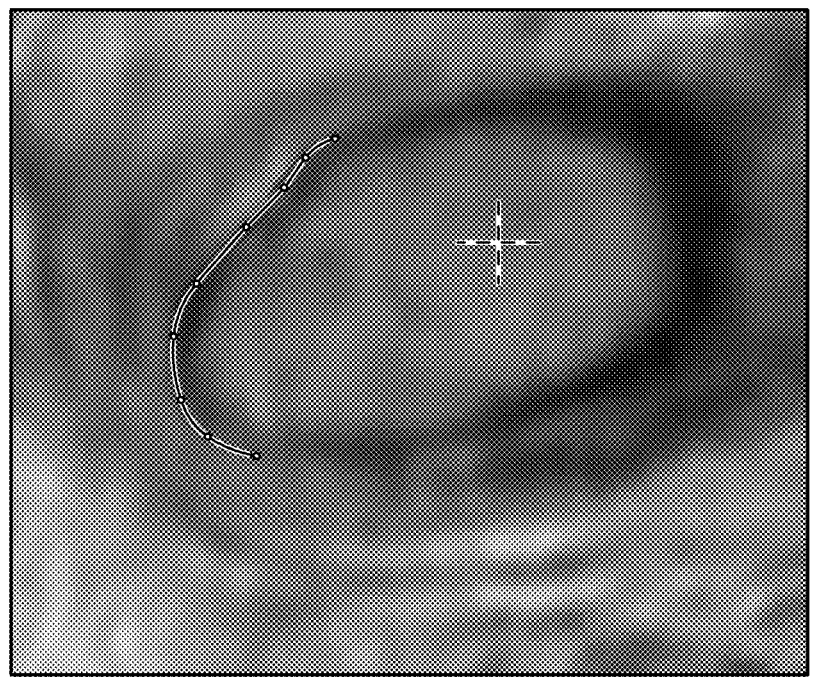

FIGS. 24A and 24B show 1st segmentation spline curve at the bottom of the major trochanter. FIGS. 25A-25C show 2nd segmentation spline curve at the root of femoral neck. (FIGS. 25B and 25C are respective posterior and anterior views in the sagittal plane.) The 1st and 2nd segmentations are performed on the same sagittal slices.

Figure 26A:
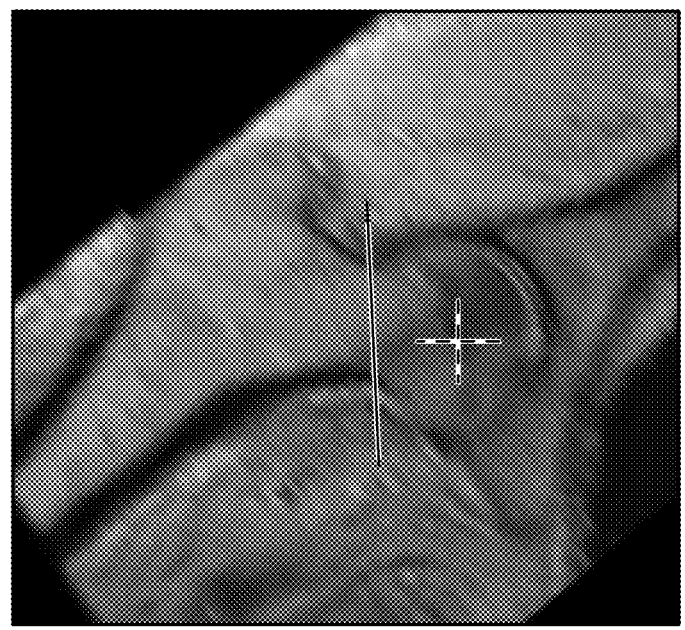
FIGS. 26A and 26B are respective coronal and sagittal views showing third segmentation splines at the mid-section of the femoral neck.
Figure 26B:
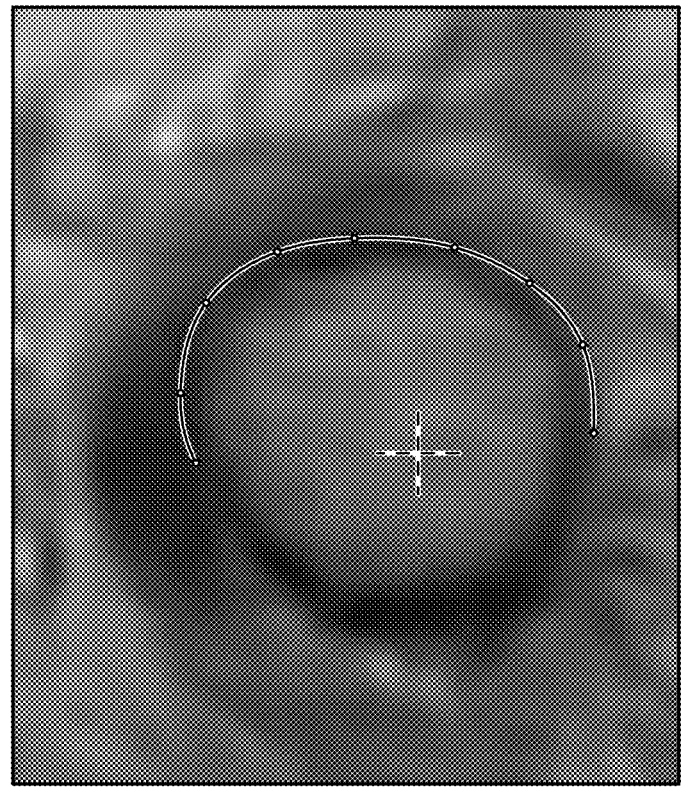

FIGS. 26A and 26B show 3rd segmentation spline curve at the mid-section of femoral neck.

Figure 27A:
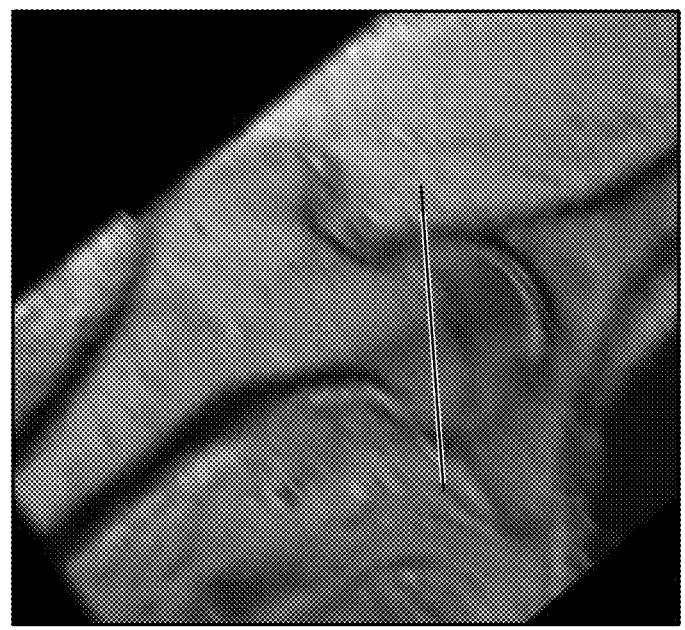
FIGS. 27A and 27B are respective coronal and sagittal views showing fourth segmentation splines at the mid-section of the femoral head.
Figure 27B:
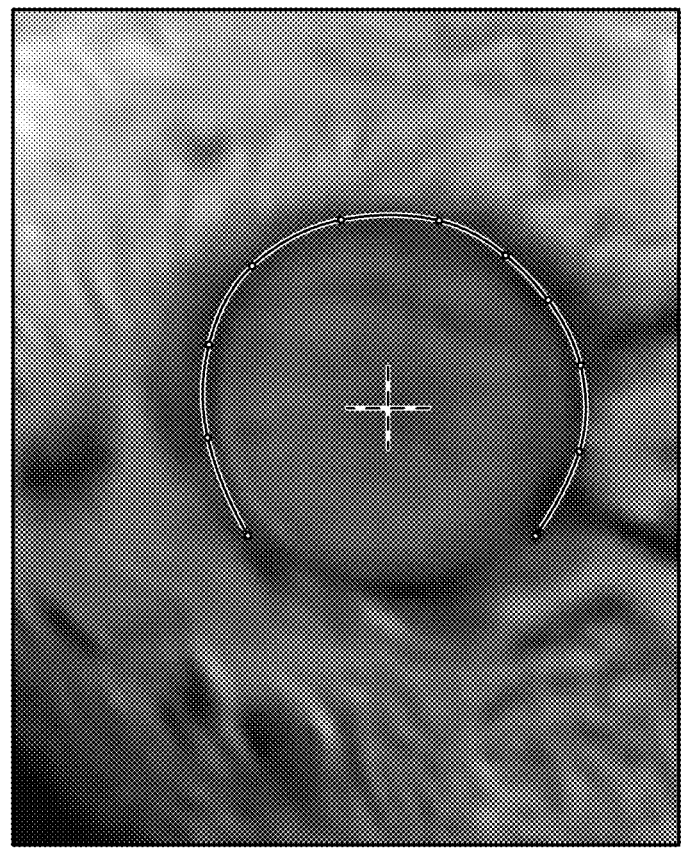

FIGS. 27A and 27B show 4th segmentation spline curve at the mid-section of femoral head.

Figure 28:
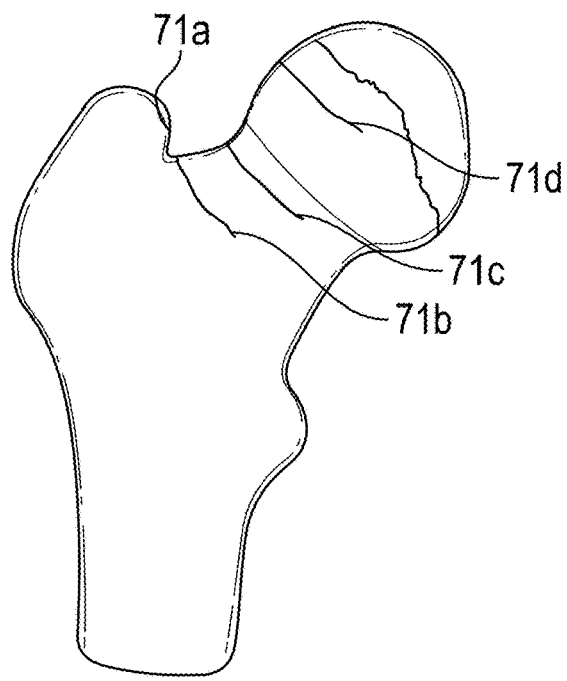
FIG. 28 is a side plan view of a proximal femur showing the locations of the respective segmentation splines from FIGS. 24-27.

FIG. 28 shows the positions of the 1st through 4th segmentation spline curves 71*a*-71*d* on the major trochanter, femoral neck and femoral head.

Figure 29A:
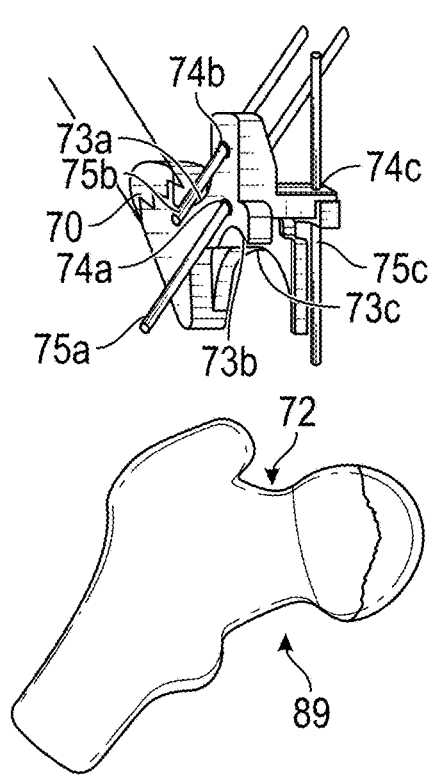
FIGS. 29A and 29B are respective posterior and anterior approaches for mating a standard hip replacement cutting guide or jig to the proximal femur.
Figure 29B:
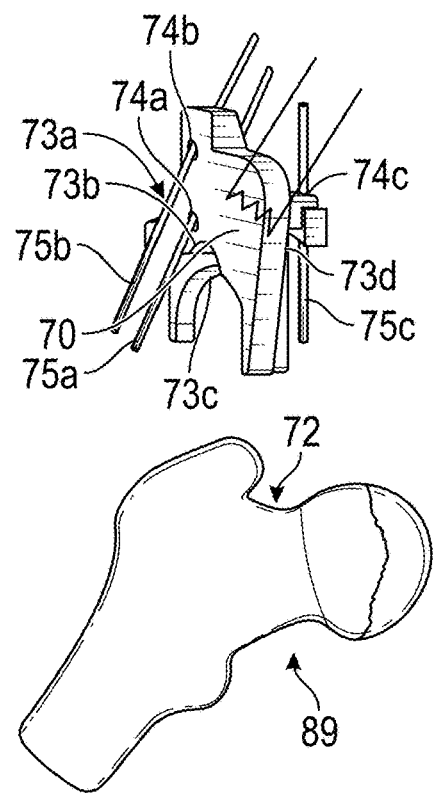

FIGS. 29A and 29B show the mating 72 of a standard total hip replacement cutting guide 70 to the proximal femur for both posterior (A) and anterior (B) approaches, respectively. The cutting guides 70 include all the segmented features 73*a*-73*d* mating on the proximal femur. In addition, there are three drilling holes 74*a*-74*c* with corresponding pins 75*a*-75*c* for fixation of the cutting guides 70. The resection tool guide features are included to assist precise resection of femoral neck.

Figure 30A:
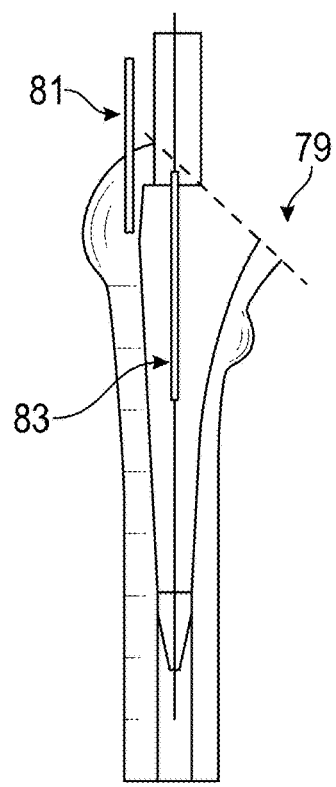
FIG. 30A is a side plan view of a broaching process to drill a cavity feature in the proximal femur after resection of the femoral neck for a standard hip replacement femoral component.
Figure 30B:
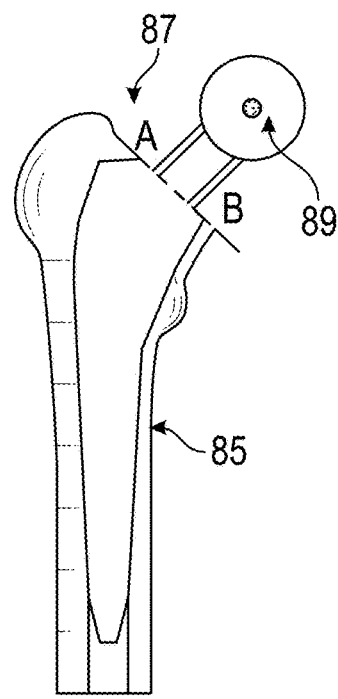
FIG. 30B is a side plan view of a standard femoral implant component inserted into the cavity feature.

FIGS. 30A and 30B show the broaching process to make cavity feature on the proximal femur. After the resection of femoral neck at plane 79, the first drilled pin 83 is removed and the drilled hole works as broaching guiding. In addition, the second pin 81, parallel to the first guiding hole, provides directional reference to the surgeons. As a result, the femoral component 85 of the total hip replacement can be placed in precision. The implant feature AB is referenced for the implant to be parallel to the resection plane 79. This approach assures the implant femoral head center 89 to be as close to the original anatomical center of the femoral head as possible.

Figure 31A:
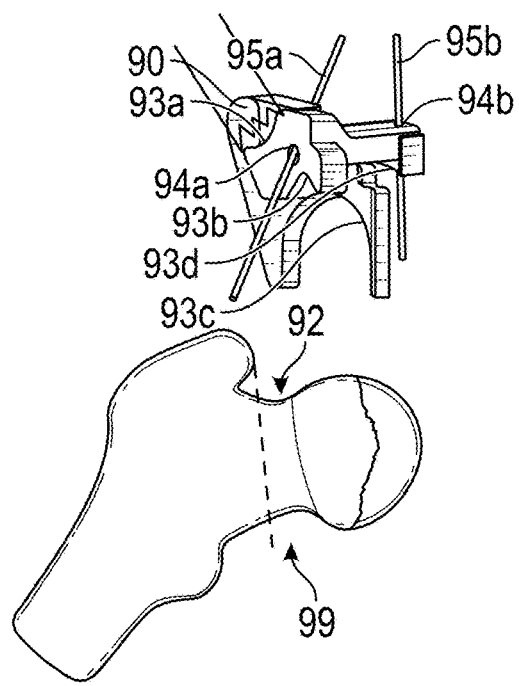
FIGS. 31A and 31B are respective posterior and anterior approaches for mating a mini or short-stem hip replacement cutting guide or jig to the proximal femur.
Figure 31B:
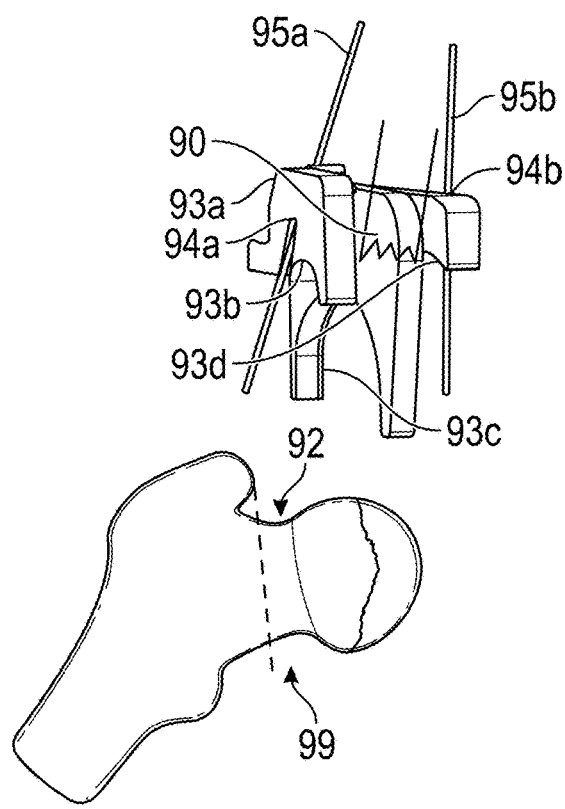

FIGS. 31A and 31B show the mating 92 of mini/short stem hip replacement cutting guide 90 to the proximal femur for both posterior (A) and anterior (B) approaches, respectively. The cutting guides 90 include all the segmented features 93a-93d mating on the proximal femur. In addition, there are two drilling holes 94a and 94b with corresponding pins 95a and 95b for fixation of the cutting guide 90. The resection tool guide features are included to assist precise resection of femoral neck.

Figure 32A:
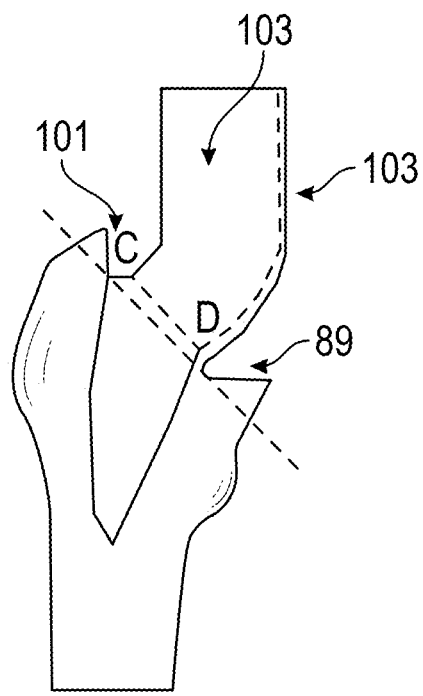
FIG. 32A is a side plan view of a broaching process to drill a cavity feature in the proximal femur after resection of the femoral neck for a mini or short-stem hip replacement femoral component.
Figure 32B:
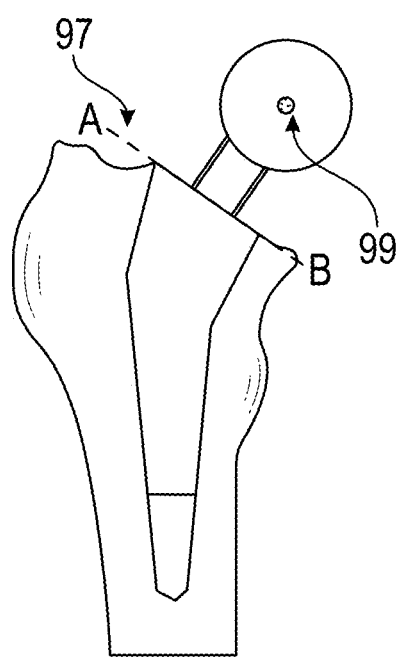
FIG. 32B is a side plan view of a mini femoral implant component inserted into the cavity feature.

FIGS. 32A and 32B show the broaching process to make cavity feature on the proximal femur with a broach tool 103. After the resection of femoral neck at plane 89, the broaching feature CD is referenced to resection plane 89. The implant is placed using implant feature AB parallel to the resection plane 89. This approach assures the implant femoral head center 99 to be as close to the original anatomical center of the femoral head as possible.

Figure 33A:
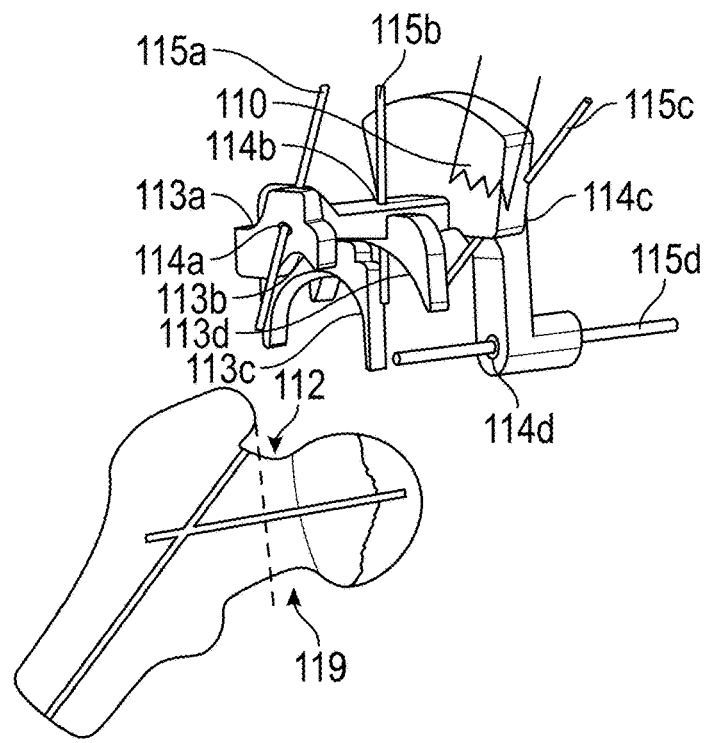
FIGS. 33A and 33B are respective posterior and anterior approaches for mating a resurfacing hip replacement cutting guide or jig to the proximal femur.
Figure 33B:
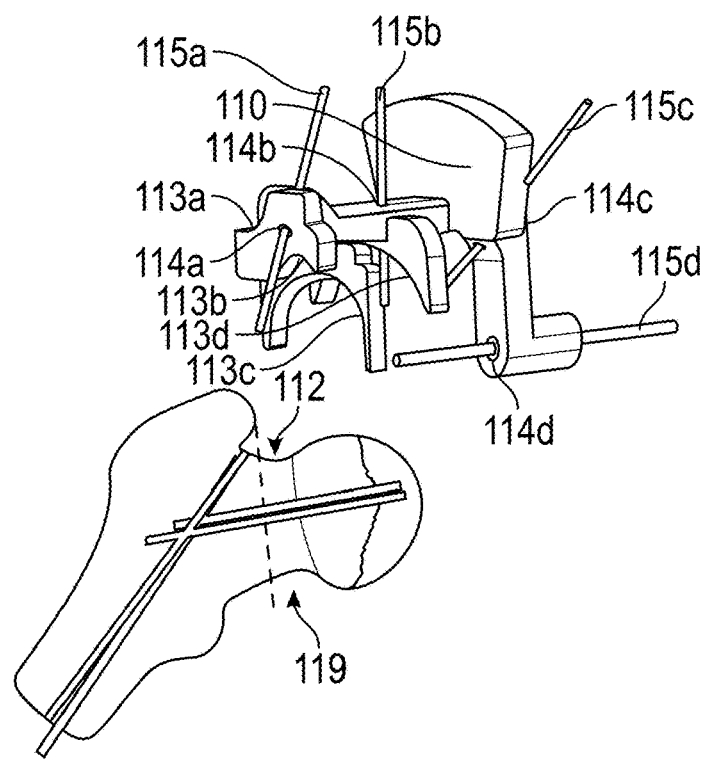

FIGS. 33A and 33B show the mating 112 of the hip resurfacing cutting guide 110 to the proximal femur for respective posterior (A) and anterior (B) approaches. The cutting guide 110 includes all the segmented features 113a-113d mating on the proximal femur. In addition, there are four drilling holes 114a-114d with corresponding pins 115-115d for fixation of the cutting guide 110. It should be noted that the hip resurfacing procedure requires that the femur be disarticulated from the hip, whereas disarticulation of femur is optional for both the hip standard and mini implant procedures.

Figure 34A:
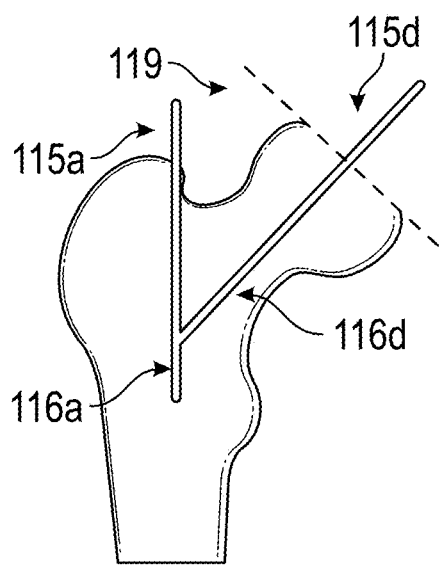
FIG. 34A is a side plan view of a pin placement in the proximal femur after resection of the femoral neck for a resurfacing hip replacement femoral component.
Figure 34B:
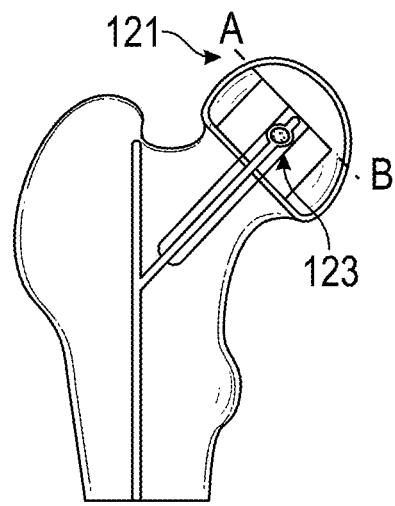
FIG. 34B is a side plan view of a standard femoral implant component inserted into the cavity feature.

FIGS. 34A and 34B show the Placement of RESURFACING femoral component. A first pin 115a and a second pin 115d are inserted into two drilled holes 116a and 116d as shown. Before the placement of resurfacing femoral component, it is confirmed that two pins 115a and 115d are intersecting each other. After confirmation, the implant is placed referenced to resection plane 119. And the implant is placed using the implant feature AB mating to the resection plane 119. This approach assures the implant femoral head center 123 will be as close to the original anatomical center of the femoral head as possible.

Acetabulum Jig Design

Figure 35:
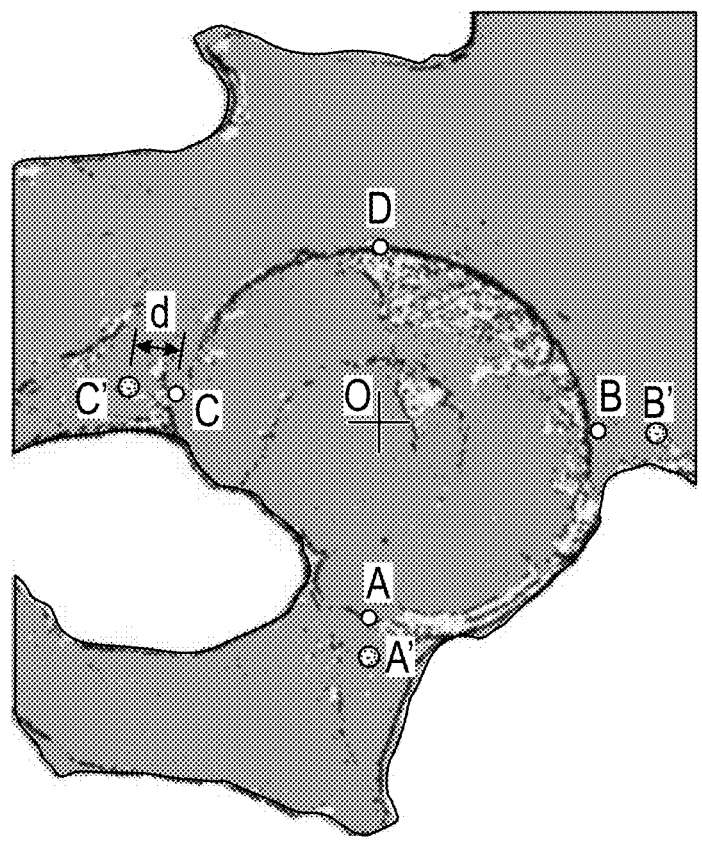
FIG. 35 shows positions of drilling holes A', B' and C' for fixation of an acetabulum cup cutting guide.

FIG. 35 illustrates the positions of drilling holes A', B' and C' for fixation of the acetabulum cup cutting guide. The acetabulum peak points A, B, and C were found in the PLANNING 1 process. The lines OA, OB and OC are extended with the distance d (2 to 4 mm) to position drilling holes of A', B' and C'.

Figure 36A:
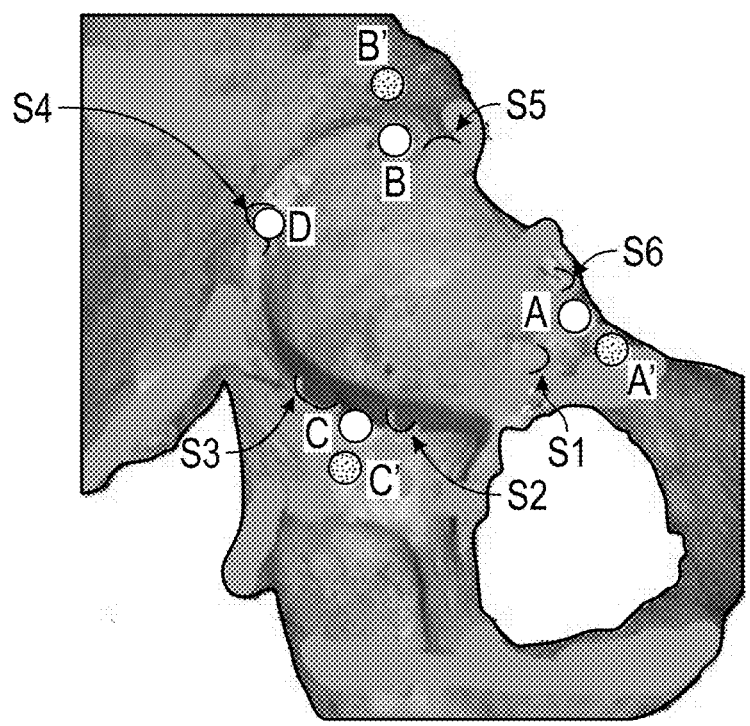
FIGS. 36A and 36B are a coronal view and schematic, respectively, of hook features S1-S6 around peak points of the pubis, ilium, and ischium and the lowest region of the acetabulum.
Figure 36B:
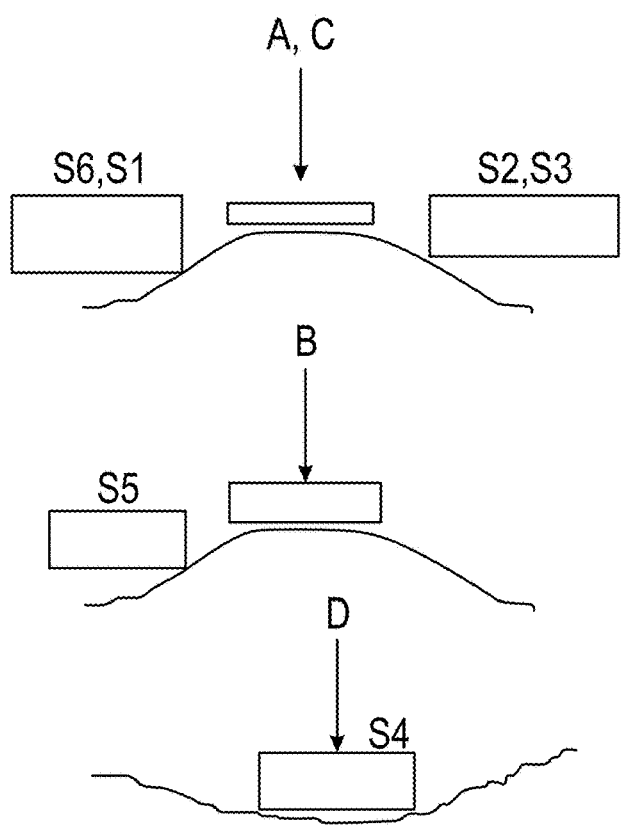
Figure 37A:
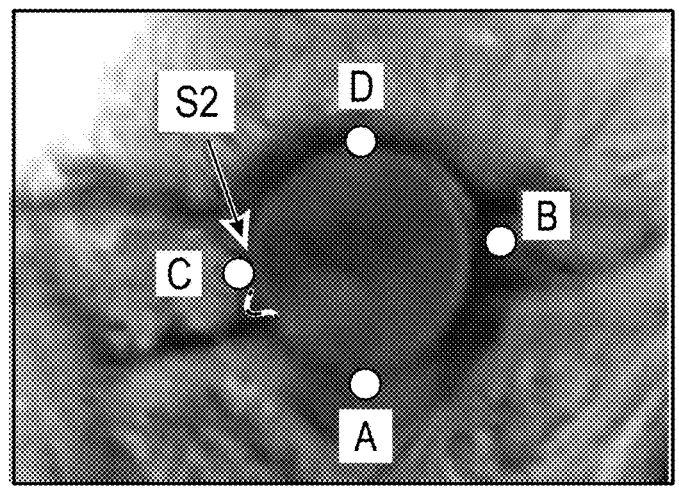
FIGS. 37A-37F are respective views of the acetabulum showing the hook featured segmentation of S1-S6, respectively.
Figure 37B:
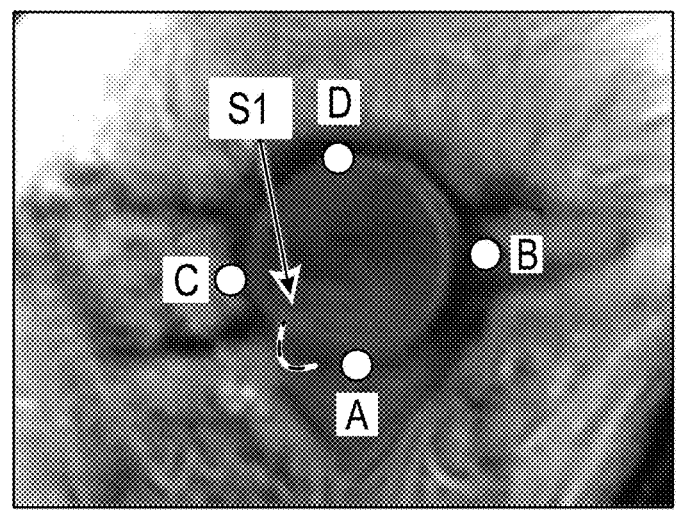
Figure 37C:
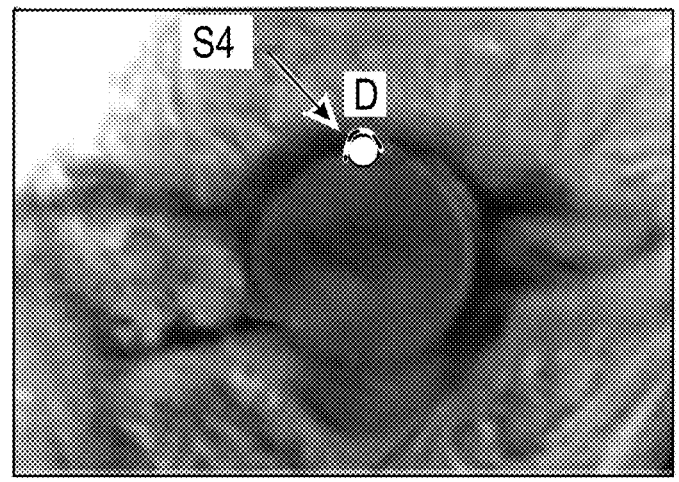
Figure 37D:
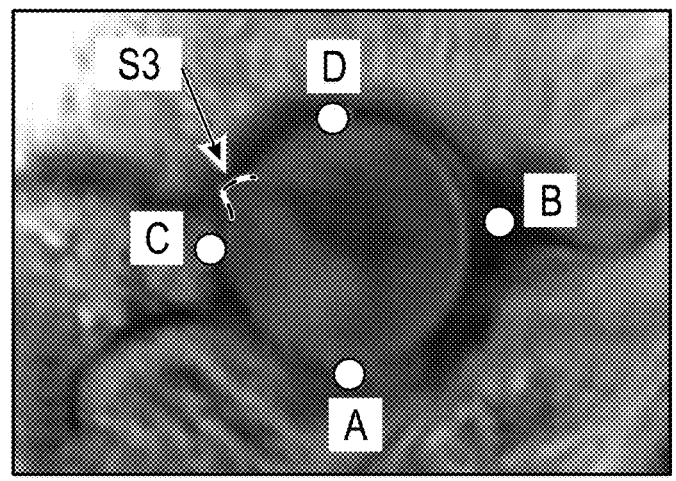
Figure 37E:
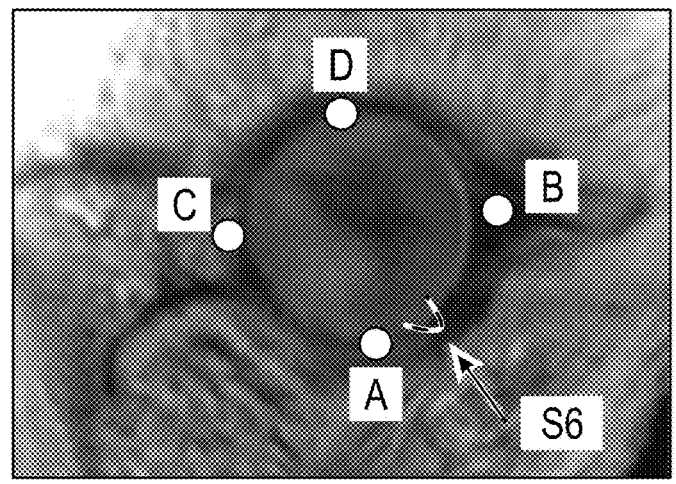
Figure 37F:
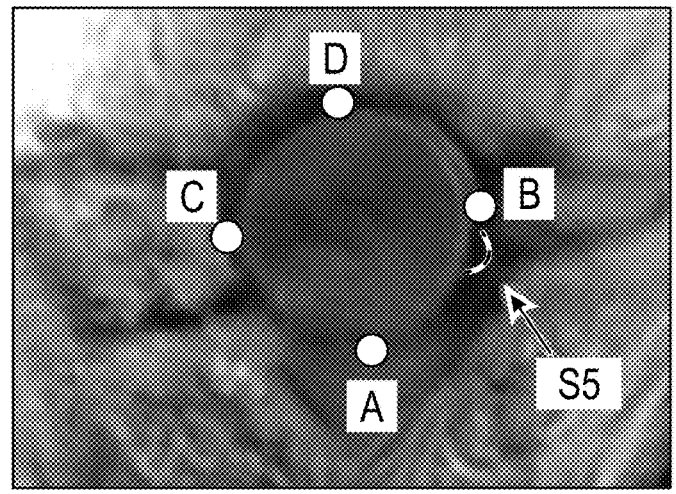

FIGS. 36A and 36B show the hook feature segmentations of S1, S2, S3, S4, S5, and S6. The points A and C are surrounded by S1, S6, S2, and S3 around peak points of the pubis and ischium, respectively. The hook features are segmented below the peak to provide a holding mechanism. The point B is hooked by S5 around the peak point of the ilium. The point D, hooked by S4, is the lowest region of the acetabulum. With three points peak contacts A, B and C along with hook features S1-S6 and the lowest reference region D, the acetabulum cup guide will be set on the acetabulum and provide precise reaming and acetabulum cup implant.

FIGS. 37A-37F show hook featured segmentation of S1, S2, S3, S4, S5, and S6.

Figure 38:
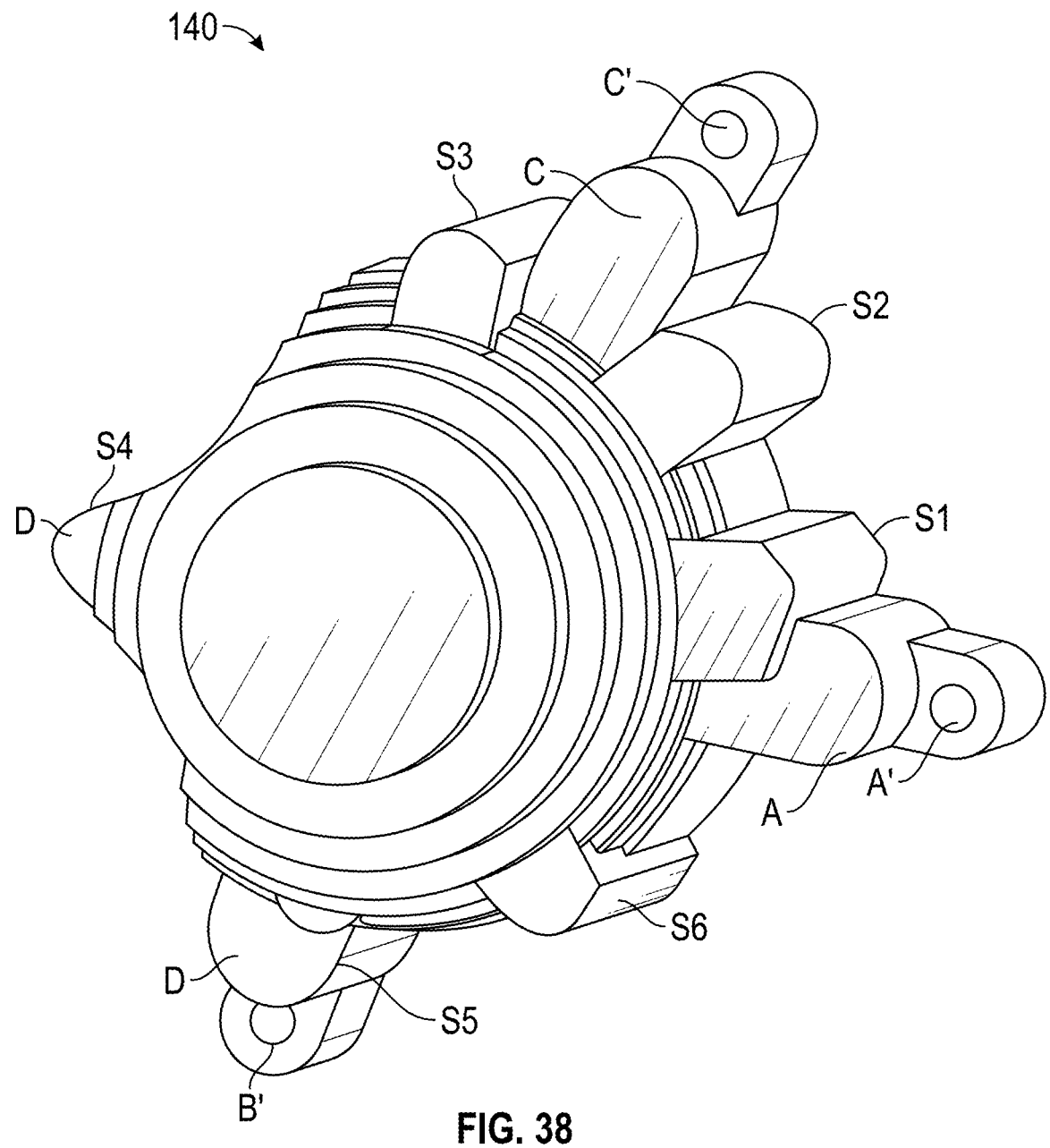
FIG. 38 is an isometric view of an acetabulum cup implant with matching peak points and hook segmentations.

FIG. 38 shows an isometric view of the acetabulum cup implant guide 140, displaying matching peak points A, B and C. Hook segmentations of S1, S2, S3, S4, S5 and S6 are featured. Also, three Drilling Holes of A', B' and C' are shown.

Figure 39A:
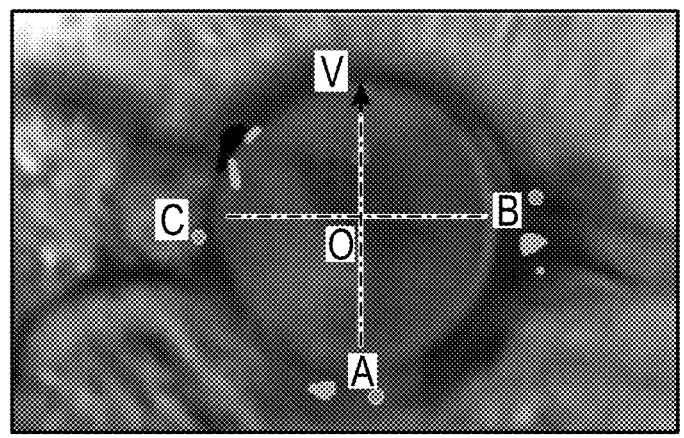
FIGS. 39A and 39B are respectively a view of the acetabulum and the cup implant showing a mating direction V.
Figure 39B:
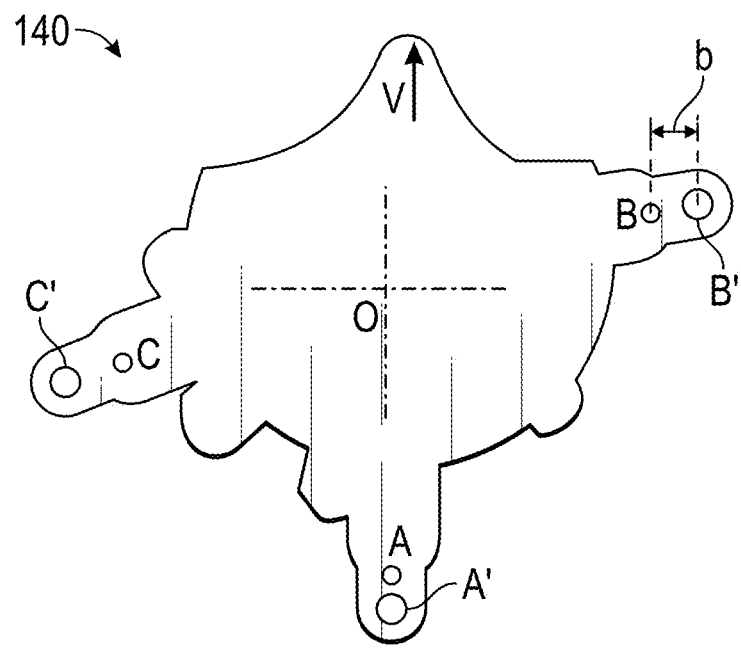

FIGS. 39A and 39B show the mating direction V with respect to the center O of the acetabulum cup jig 140, the anatomical points A, B and C and guide holes A', B' and C'.

Figure 40:
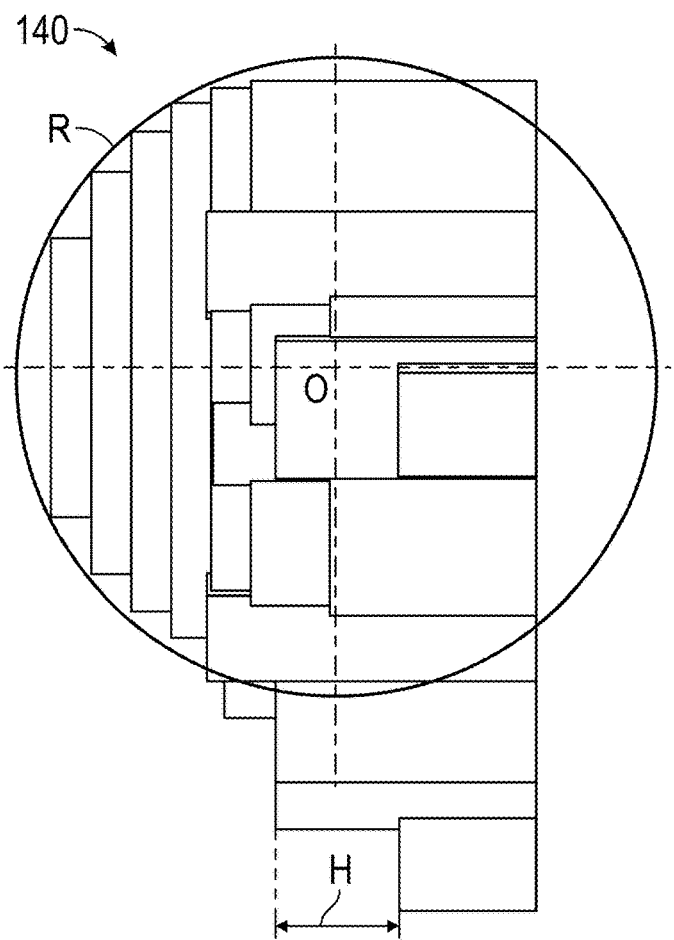
FIG. 40 is a side plan view of the acetabulum cup implant showing a step feature corresponding to a radius R of the acetabulum.

FIG. 40 shows the step feature with radius R, a radius of acetabulum cup size, is introduced to match the inside of the anatomical cup feature. The drilling holes are designed with a height h (>5 mm) above the peak contact points A, B and C to avoid any interference against surrounding anatomy of the acetabulum.

Figure 41:
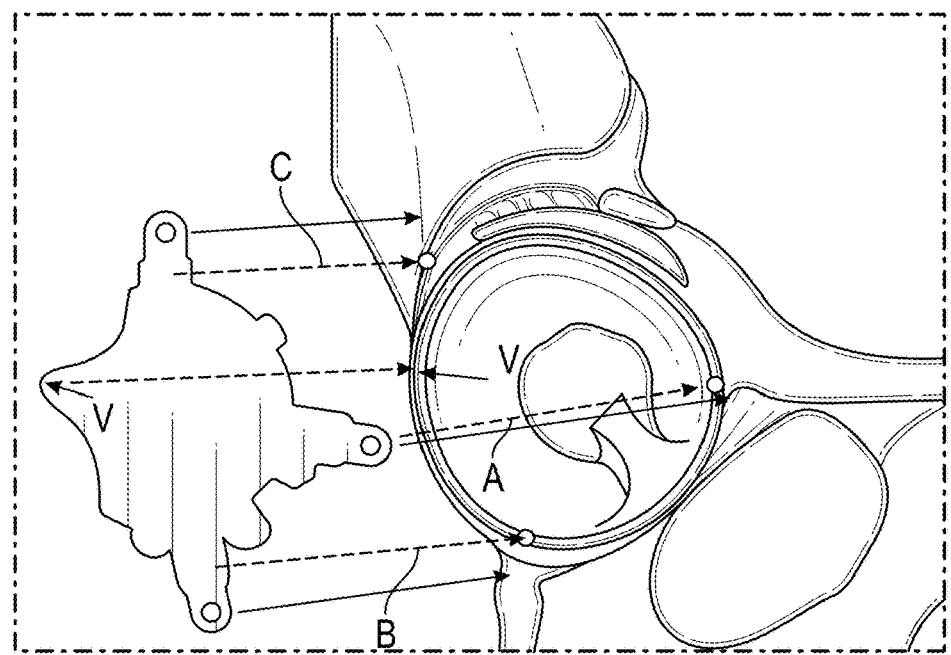
FIG. 41 shows direction and orientation of mating of the surgical jig onto the acetabulum cup.

FIG. 41 shows the direction and orientation of jig mating 140 onto the acetabulum cup. The three holes guide the pins relative to the peak points A, B and C on the acetabular rim for fixation and the acetabulum cup placement direction.

Figure 42:
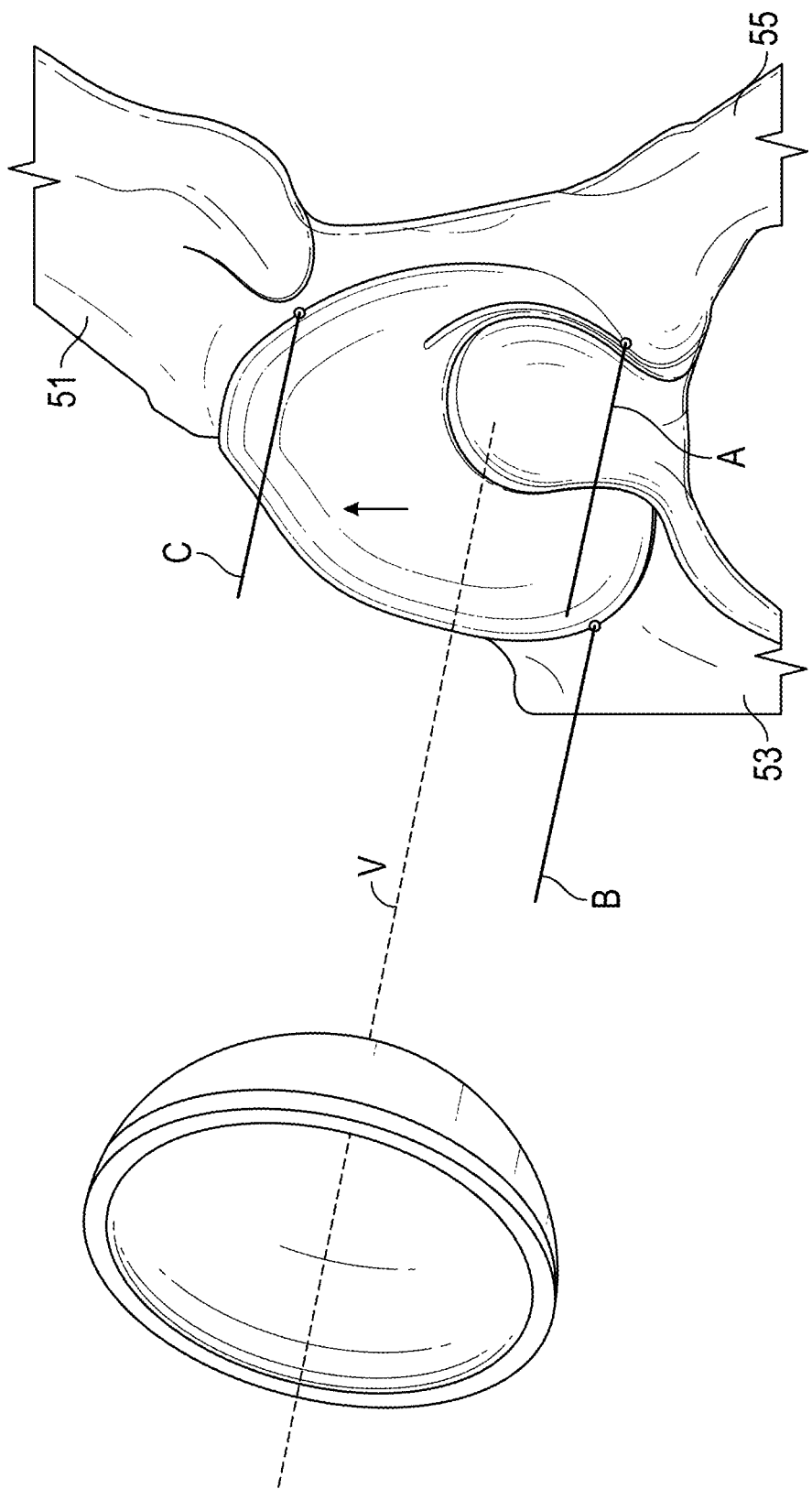
FIG. 42 is a perspective view of a hip acetabulum anatomy with surgical guiding pins A, B and C for an acetabulum cup implant.

FIG. 42 shows that at least three pins corresponding to peak acetabulum points A, B and C provide not only a reaming guiding direction but also implant positioning guiding direction V. The number of guiding pins is the surgeon's decision. The ilium 51, ischium 53 and pubis 55 of the hip are indicated for reference.

The invention claimed is:

1. A computer-aided method using a pre-operative planning tool for establishing, from patient-specific images, femoral and acetabular implant sizes and cut planes for hip joint replacement, comprising:
obtaining, and inputting as image data into a computer, a set of coronal, axial, and sagittal images of a hip joint of a patient, as well as image slices along an axis of a femoral neck of the patient;
marking, through user interaction with the pre-operative planning tool in the computer, coordinate positions of a set of selected points in the image data of a proximal femur and an acetabulum, wherein the selected acetabulum points include pubis, ilium and ischium high points;
performing by the pre-operative planning tool in the computer a best fit of available implants to the set of selected proximal femur and acetabulum points to offer a range of suitable implant and surgical cut plane parameters for selection by a surgeon; and
constructing patient-specific surgical jigs for the proximal femur and the acetabulum of the hip joint in accord with the surgeon-selected parameters;
wherein the constructed proximal femur patient-specific surgical jig is used for resecting the proximal femur and includes a set of segmented features mating against surfaces of the proximal femur in a unique position, the segmented features being determined from overlaying segmentation spline curves onto coronal and sagittal views of the image data for a femoral head, the femoral neck, and a major trochanter of the proximal femur; and
wherein the constructed acetabulum patient-specific surgical jig is used for reaming the acetabulum and includes a set of at least three drilling holes for receiving pins for fixing the acetabulum patient-specific surgical jig at points at specified distance outside of the pubis, ilium and ischium high points of a rim of the acetabulum, coordinates for the three high points being established from sagittal views of the image data of the acetabulum of the hip joint, the jig being fixed relative to a plane defined by those three high points of the rim of the acetabulum.

2. The method as in claim 1, wherein marking the coordinate positions includes overlaying and adjusting a circle icon over the coronal views, axial views and the sagittal views of the image data for the femoral head to determine a center point of the femoral head in each of the views to serve as a reference coordinate origin for all subsequent markings of coordinate positions of the selected proximal femur and acetabulum points in the image data.

3. The method as in claim 1, wherein the selected points of the proximal femur include a center and a radius of the femoral head, a point of the major trochanter and a midpoint of the femoral shaft.

4. The method as in claim 1, wherein the selected acetabulum points also include a lowest point on the rim of the acetabulum.

5. The method as in claim 1, wherein the patient-specific surgical jigs as constructed also correspond to a surgeon selection between standard, mini, short-stem, and resurfacing hip replacement femoral component.

6. The method as in claim 1, wherein the constructed proximal femur patient-specific surgical jig provides an established cut plane based upon femoral shaft and femoral neck reference lines identified from a center of the femoral head, a midpoint of the major trochanter and a femoral shaft midpoint coordinates in at least axial and sagittal views of the image data of the proximate femur, the femoral shaft reference line extending through the major trochanter midpoint and the femoral shaft midpoint, and the femoral neck reference line extending through the major trochanter midpoint and the femoral head center, the cut plane being perpendicular to the established femoral neck reference line.

7. The method as in claim 1, wherein a first of the segmentation spline curves is formed at a bottom of the major trochanter, a second of the segmentation spline curves is formed at a root of the femoral neck, a third of the segmentation spline curves is formed at a midsection of the femoral neck, and a fourth of the segmentation spline curves is formed at a midsection of the femoral head.

8. The method as in claim 1, wherein the constructed proximal femur patient-specific surgical jig includes a set of drill pins extending through holes formed in the constructed proximal femur patient-specific surgical jig that form broaching guide holes into the proximal femur and parallel directional reference for broaching the proximal femur.

9. The method as in claim 1, wherein the constructed acetabulum patient-specific surgical jig includes a fourth drilling hole at a specified distance outside of a lowest point of the acetabulum rim.

10. The method as in claim 1, wherein the constructed acetabulum patient-specific surgical jig includes a set of hook feature segmentations that serve as a holding mechanism for the constructed acetabulum patient-specific surgical jig while drilling through the drilling holes of the constructed acetabulum patient-specific surgical jig, coordinates for the hook feature segmentations being established from at least coronal views of the image data of the acetabulum of the hip joint.

11. The method as in claim 1, wherein the constructed acetabulum patient-specific surgical jig has a stepped reaming guide radius corresponding to a radius of the acetabulum established by overlaying and adjusting a circle icon over coronal, axial and sagittal views of the image data of the acetabulum.

12. A computer-aided method using a pre-operative planning tool for establishing, from patient-specific images, femoral and acetabular implant sizes and cut planes for hip joint replacement, comprising:

obtaining, and inputting as image data into a computer, a set of coronal, axial, and sagittal images of a hip joint of a patient, as well as image slices along an axis of a femoral neck of the patient;

marking, through user interaction with the pre-operative planning tool in the computer, coordinate positions of a set of selected points in the image data of a proximal femur and an acetabulum, the selected proximal femur points including a femoral head center, a major trochanter midpoint and a femoral shaft midpoint, the selected acetabulum points including pubis, ilium and ischium high points and an acetabulum rim lowest point;

performing by the pre-operative planning tool in the computer a best fit of available implants to the set of selected proximal femur and acetabulum points to offer a range of suitable implant options and surgical cut plane parameters for selection by a surgeon; and constructing patient-specific surgical jigs for the proximal femur and the acetabulum of the hip joint in accord with surgeon-selected parameters, the implant options including standard, mini, short-stem, and resurfacing hip replacement, the constructed proximal femur patient-specific surgical jig is used for resecting the proximal femur and providing an established cut plane based upon established femoral shaft and femoral neck reference lines identified from the femoral head center, the major trochanter midpoint and the femoral shaft midpoint coordinates, the femoral shaft reference line extending through the major trochanter midpoint and the femoral shaft midpoint, and the femoral neck reference line extending through the major trochanter midpoint and the femoral head center, the cut plane being perpendicular to the established femoral neck reference line;

wherein the constructed proximal femur patient-specific surgical jig includes a set of segmented features mating against surfaces of the proximal femur in a unique position, the segmented features being determined from overlaying segmentation spline curves onto coronal and sagittal views of the image data of the femoral head, the femoral neck, and the major trochanter; and wherein the constructed acetabulum patient-specific surgical jig is used for acetabulum reaming and includes a set of at least three drilling holes for receiving pins for fixing the acetabulum patient-specific surgical jig at points at specified distance outside of the pubis, ilium and ischium high points of the rim of the acetabulum, coordinates for the three high points being established from sagittal views of the image data of the acetabulum of the hip joint, the constructed acetabulum patient-specific jig being fixed relative to a plane defined by those three high points of the rim.

13. The method as in claim 12, wherein marking the coordinate positions includes overlaying and adjusting a circle icon over the coronal views, axial views and the sagittal views of the image data for the femoral head to determine a center point of the femoral head in each of the views to serve as a reference coordinate origin for all subsequent markings of coordinate positions of the selected proximal femur and acetabulum points in the image data.

14. The method as in claim 12, wherein a first of the segmentation spline curves is formed at a bottom of the major trochanter, a second of the segmentation spline curves is formed at a root of the femoral neck, a third of the segmentation spline curves is formed at a midsection of the femoral neck, and a fourth of the segmentation spline curves is formed at a midsection of the femoral head.

15. The method as in claim 12, wherein the constructed acetabulum patient-specific surgical jig includes a set of hook feature segmentations that serve as a holding mechanism for the constructed acetabulum patient-specific surgical jig while drilling through the drilling holes of the constructed acetabulum patient-specific surgical jig, coordinates for the hook feature segmentations being established from at least coronal views of the image data of the acetabulum of the hip joint.

16. The method as in claim 12, wherein the constructed acetabulum patient-specific surgical jig has a stepped reaming guide radius corresponding to a radius of the acetabulum established by overlaying and adjusting a circle icon over coronal, axial and sagittal views of the image data of the acetabulum.

* * * * *